(12) United States Patent
Singh et al.

(10) Patent No.: US 9,753,379 B2
(45) Date of Patent: Sep. 5, 2017

(54) INSPECTION APPARATUS AND METHODS, METHODS OF MANUFACTURING DEVICES

(71) Applicant: ASML Netherlands B.V., Veldhoven (NL)

(72) Inventors: Amandev Singh, Eindhoven (NL); Henricus Petrus Maria Pellemans, Veldhoven (NL); Patrick Warnaar, Tilburg (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 14/794,013

(22) Filed: Jul. 8, 2015

(65) Prior Publication Data

US 2016/0011523 A1 Jan. 14, 2016

(30) Foreign Application Priority Data

Jul. 9, 2014 (EP) .................................... 14176391

(51) Int. Cl.
*G03B 27/52* (2006.01)
*G03B 27/32* (2006.01)
(Continued)

(52) U.S. Cl.
CPC ........ *G03F 7/70491* (2013.01); *G01J 3/2823* (2013.01); *G01J 3/45* (2013.01);
(Continued)

(58) Field of Classification Search
CPC ....... G01N 21/4788; G01N 2201/06113; G01J 3/2823; G01J 3/2826; G01J 3/2813;
(Continued)

(56) References Cited

U.S. PATENT DOCUMENTS

| 5,923,423 A | 7/1999 | Sawatari et al. |
| 6,034,378 A * | 3/2000 | Shiraishi ................... G03F 9/70 250/237 G |

(Continued)

FOREIGN PATENT DOCUMENTS

| WO | WO 2012/126718 A1 | 9/2012 |
| WO | WO 2013/178422 A1 | 12/2013 |
| WO | WO 2014/082938 A1 | 6/2014 |

OTHER PUBLICATIONS

International Search Report directed to related International Patent Application No. PCT/EP2015/063828, mailed Sep. 16, 2015; 2 pages.

(Continued)

*Primary Examiner* — Christina Riddle
(74) *Attorney, Agent, or Firm* — Sterne, Kessler, Goldstein & Fox P.L.L.C.

(57) ABSTRACT

Inspection apparatus (100) is used for measuring parameters of targets on a substrate. Coherent radiation follows an illumination path (solid rays) for illuminating target (T). A collection path (dashed rays) collects diffracted radiation from the target and delivers it to a lock-in image detector (112). A reference beam following a reference path (dotted rays). An acousto-optical modulator (108) shifts the optical frequency of the reference beam so that the intensity of radiation at the lock-in detector includes a time-varying component having a characteristic frequency corresponding to a difference between the frequencies of the diffracted radiation and the reference radiation. The lock-in image detector records two-dimensional image information representing both amplitude and phase of the time-varying component. A second reference beam with a different shift (110)

(Continued)

follows a second reference path (dot-dash rays). Interference between the two reference beams can be used for intensity normalization.

24 Claims, 10 Drawing Sheets

(51) Int. Cl.
    *G03F 7/20*     (2006.01)
    *G01J 3/28*     (2006.01)
    *G01J 3/45*     (2006.01)
    *G01N 21/47*     (2006.01)

(52) U.S. Cl.
    CPC ..... *G01N 21/4788* (2013.01); *G03F 7/70625* (2013.01); *G03F 7/70633* (2013.01); *G01N 2201/06113* (2013.01)

(58) Field of Classification Search
    CPC ........ G01J 3/282; G01J 3/2886; G01J 3/2889; G01J 3/45; G01J 3/451; G01J 3/453; G01J 3/4538; G03F 7/70491; G03F 7/70525; G03F 7/70533; G03F 7/70625; G03F 7/70633; G03F 7/70666; G03F 7/70675; G03F 7/70683; G03F 7/7085
    USPC ............... 355/52, 53, 55, 67–71, 72–75, 77; 356/4.09, 4.1, 5.09, 5.11, 5.12, 5.13, 319, 356/320, 323, 451, 484, 485, 489, 490, 356/496, 500, 508, 509, 511, 625, 634, 356/636; 250/492.1, 492.2, 492.21, 250/492.23, 493.1, 548
    See application file for complete search history.

(56) References Cited

U.S. PATENT DOCUMENTS

| | | | |
|---|---|---|---|
| 6,479,200 B1* | 11/2002 | Stirton | G03F 7/70616 430/30 |
| 7,088,451 B2 | 8/2006 | Sezginer | |
| 7,339,170 B2 | 3/2008 | Deliwala | |
| 7,397,596 B2 | 7/2008 | Yacoubian | |
| 7,403,293 B2 | 7/2008 | Pellemans et al. | |
| 7,466,429 B2* | 12/2008 | de Groot | G01B 11/0675 356/497 |
| 7,791,727 B2* | 9/2010 | Den Boef | G03F 7/70341 356/401 |
| 2004/0042014 A1 | 3/2004 | Feldman | |
| 2006/0033921 A1 | 2/2006 | Den Boef et al. | |
| 2008/0036984 A1 | 2/2008 | Mos et al. | |
| 2009/0262335 A1* | 10/2009 | Ukraintsev | G01B 9/021 356/73 |
| 2010/0128279 A1* | 5/2010 | Cho | G01B 9/02003 356/484 |
| 2010/0201963 A1 | 8/2010 | Cramer et al. | |
| 2010/0328655 A1 | 12/2010 | Den Boef | |
| 2011/0027704 A1 | 2/2011 | Cramer et al. | |
| 2011/0043791 A1 | 2/2011 | Smilde et al. | |
| 2011/0069292 A1 | 3/2011 | Den Boef | |
| 2011/0102753 A1 | 5/2011 | Van De Kerkhof et al. | |
| 2012/0044470 A1 | 2/2012 | Smilde et al. | |
| 2012/0123581 A1 | 5/2012 | Smilde et al. | |
| 2012/0243004 A1 | 9/2012 | El Gawhary et al. | |
| 2013/0258310 A1 | 10/2013 | Smilde et al. | |
| 2013/0271740 A1 | 10/2013 | Quintanilha | |
| 2014/0139814 A1 | 5/2014 | Cramer et al. | |

OTHER PUBLICATIONS

"Acousto-optic modulator," Wikipedia.org., accessed at http://en.wikipedia.org/wiki/Acousto-optic_modulator on Jun. 6, 2014; 3 pages.
Balistreri, M.L.M, et al., "Phase Mapping of Optical Fields in Integrated Optical Waveguide Structures," Journal of Lightwave Technology, vol. 19, No. 8, Aug. 2001; pp. 1169-1176.
Destouches, N., et al., "Determination of the phase of the diffracted field in the optical domain: Application to the reconstruction of surface profiles," Optics Communications, vol. 198, Nov. 2001; pp. 233-239.
Foix, S., et al., "Lock-in Time-of-Flight (ToF) Cameras: A Survey," IEEE Sensors Journal, vol. 11, No. 3, Mar. 2011; pp. 1-11.
El Gawhary, O., et al., "Performance analysis of Coherent Optical Scatterometry," Applied Physics B, vol. 105, Dec. 2011; 13 pages.
Kumar, N., et al., "Phase retrieval between overlapping orders in coherent Fourier scatterometry using scanning," Journal of European Optical Society Rapid Publications, vol. 8, 2013; pp. 13048-1 to 13048-8.
Lange, R., et al., "Solid-State Time-of-Flight Range Camera," IEEE Journal of Quantum Electronics, vol. 37, No. 3, Mar. 2001; pp. 390-397.
Pitter, M., et al., "CMOS cameras for phase sensitive imaging," Institute of Biophysics, Imaging and Optical Science, University of Nottingham, Institute of 2010; 33 pages.
Pitter, M.C., et al., "Full-field heterodyne interference microscope with spatially incoherent illumination," Optics Letters, vol. 29, No. 11, Jun. 1, 2004; pp. 1200-1202.
Sommargren, G.E., "Optical heterodyne profilometry," Applied Optics, vol. 20, No. 4, Feb. 15, 1981; pp. 610-618.
International Preliminary Report on Patentability and Written Opinion of the International Searching Authority, directed to Application No. PCT/EP2015/063828, issued Jan. 10, 2017; 7 pages.

* cited by examiner

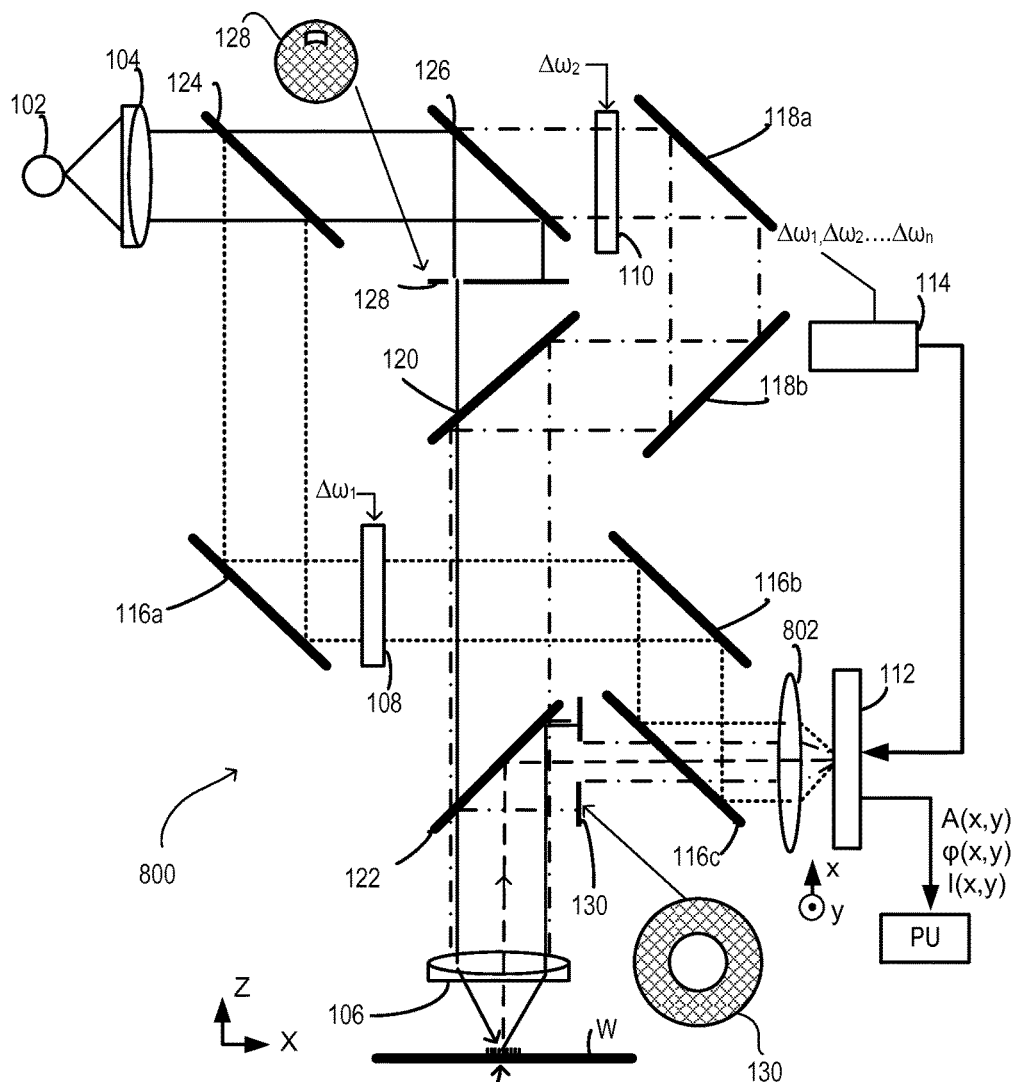
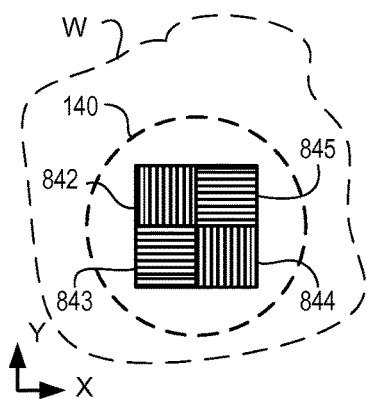
Fig 8B
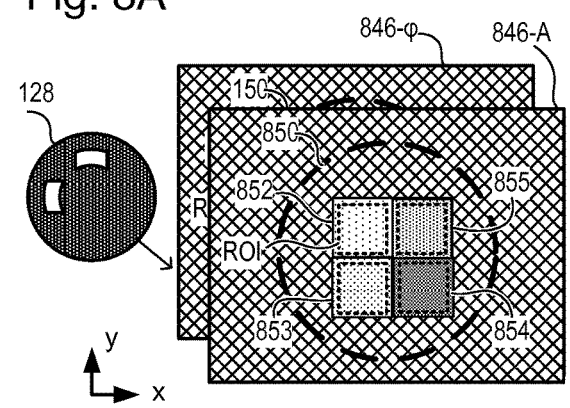
Fig 8C
Fig. 8A

INSPECTION APPARATUS AND METHODS, METHODS OF MANUFACTURING DEVICES

CROSS REFERENCE TO RELATED APPLICATIONS

This application claims benefit of EP Patent Application No 14176391.2, filed on Jul. 9, 2014.

FIELD

The present invention relates to inspection apparatus and associated method of inspection usable, for example, in the manufacture of devices by lithographic techniques. The invention further relates to methods of manufacturing devices and to computer program products useful in implementing such methods.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay (the accuracy of alignment between patterns formed in different patterning steps, for example between two layers in a device) and defocus of the lithographic apparatus. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target structure by iterative approaches such as rigorous coupled wave analysis or finite element methods; library searches; and principal component analysis.

Methods and apparatus for determining structure parameters are, for example, disclosed in WO 20120126718. Methods and scatterometers are also disclosed in US20110027704A1, US2006033921A1 and US2010201963A1. The targets used by such scatterometers are relatively large, e.g., 40 µm by 40 µm, gratings and the measurement beam generates an illumination spot that is smaller than the grating (i.e., the grating is underfilled). In addition to scatterometry to determine parameters of a structure made in one patterning step, the methods and apparatus can be applied to perform diffraction-based overlay measurements.

Diffraction-based overlay metrology using dark-field image detection of the diffraction orders enables overlay measurements on smaller targets. These targets can be smaller than the illumination spot and may be surrounded by product structures on a wafer. Multiple targets can be measured in one image. Examples of dark-field imaging metrology can be found in international patent applications US2010328655 A1 and US2011069292 A1 which documents are hereby incorporated by reference in their entirety. Further developments of the technique have been described in published patent publications US20110027704A, US20110043791A, US20120044470A US20120123581A, US20130258310A, US20130271740A and WO2013178422A1. These targets can be smaller than the illumination spot and may be surrounded by product structures on a wafer. Multiple gratings can be measured in one image, using a composite grating target. Similar techniques have been developed for measurement of focus and dose using modified small targets. Methods of determining dose and focus of a lithographic apparatus are disclosed in documents WO2014082938 A1 and US2014/0139814A1, respectively. The contents of all the mentioned applications are also incorporated herein by reference.

Therefore, in known intensity-based scatterometers parameters of interest such as overlay, CD and focus are inferred by measuring the intensity of radiation diffracted by appropriate targets. For example, in diffraction-based metrology using dark-field imaging, results are obtained by measuring the target in such a way as to obtain separately the −1st and the +1st diffraction order intensities. Comparing these intensities for a given grating provides a measurement of asymmetry in the target. The measured asymmetry can then be converted to a measurement of overlay, focus or dose, depending on the form of the target, which is specifically designed to have an asymmetry that is sensitive to the parameter of interest.

The known examples and methods measure only the intensity of scattered radiation using incoherent light sources. Reconstruction of the target is an ill-posed inverse problem which cannot be solved without prior information about the target. To solve the ill-posed inverse problem when using current inspection apparatuses, relatively large target structures are required for the extraction of parameters of interest. Similarly, the known dark-field imaging metrology with small targets measures only the intensity of different diffraction orders, and measurements are undesirably sensitive to process-induced variations. That is to say, the measurement does not distinguish between asymmetry due to the parameter of interest and asymmetry or other variations caused by process variations.

In US2012243004A1 it is proposed to adapt a scatterometer of the type described above to perform coherent Fourier scatterometry. The aim of this modification is obtain phase information of the diffraction spectrum, as well as intensity information. The availability of phase information allows a more confident reconstruction. The method disclosed in US2012243004A1 requires multiple diffraction spectra to be captured and compared to obtain the phase information. Therefore it incurs a penalty in throughput, that is to say fewer measurements can be made in a given time. In a high-volume manufacturing environment, throughput as well as accuracy should be maximized.

SUMMARY

The invention aims to provide optical inspection apparatus and metrology methods that can obtain and exploit phase information from diffraction spectra, while being more suitable for use in high-volume manufacturing environments.

The invention in a first aspect provides an inspection apparatus for measuring properties of a targets structure, the apparatus comprising a radiation source, and an image detector in combination with an optical system, the optical system defining the following beam paths:
an illumination path for receiving radiation from the radiation source, forming a beam of illuminating radiation having a selected illumination profile and focusing said illuminating radiation onto a target on a substrate;
a collection path for collecting diffracted radiation from said target and delivering a selected portion of the diffracted radiation to the image detector; and
a reference path for receiving radiation from the radiation source and delivering a beam of reference radiation to the image detector so as to interfere with the diffracted radiation,
wherein the image detector comprises an array of pixels for capturing two-dimensional images,
wherein at least one of said illumination path and said reference path includes a device for shifting an optical frequency of the reference radiation so that the intensity of radiation at the image detector includes a time-varying component having a characteristic frequency corresponding to a difference between the frequencies of the diffracted radiation and the reference radiation,
and wherein said image detector comprises a lock-in image detector operable with reference to said characteristic frequency to record for each pixel information representing both amplitude and phase of said time-varying component.

The apparatus in some embodiments includes a processor for processing the recorded amplitude and phase information to calculate a measurement of a property of the target.

The apparatus in some embodiments is operable to calculate measurements of asymmetry for multiple targets. The processor may be further arranged to calculate using said measurements and known characteristics of the targets a performance parameter of a lithographic process used to form the targets. The performance parameter may be for example one of overlay, focus and dose.

The lock-in image detector may be located in a pupil plane or in an image plane of the collection path.

The invention in another aspect provides a method for measuring properties of a targets structure, the method comprising the steps:
(a) illuminating a target on a substrate with an illuminating radiation emitted from a radiation source and having a selected illumination profile;
(b) collecting diffracted radiation from said target and delivering a selected portion of the diffracted radiation to an image detector comprising an array of pixels for capturing two-dimensional images;
(c) delivering a beam of reference radiation emitted from the radiation source to the image detector so as to interfere with the diffracted radiation,
wherein steps (a) and (c) include introducing an optical frequency shift between the reference radiation and the illuminating radiation so that the intensity of radiation at the image detector includes a time-varying component having a characteristic frequency corresponding to the frequency shift; and wherein step (b) includes operating the image detector as a lock-in image detector at the characteristic frequency, to record two-dimensional images both amplitude and phase of the time-varying component.

The invention yet further provides a method of manufacturing devices wherein device features and metrology targets are formed on a series of substrates by a lithographic process, wherein properties of the metrology targets on one or more processed substrates are measured by a method or inspection apparatus according to the invention as set forth above, and wherein the measured properties are used to adjust parameters of the lithographic process for the processing of further substrates.

The invention in other aspects provides computer program products containing one or more sequences of machine-readable instructions for implementing steps of the method of one or more embodiments. The computer program product may comprise a said instructions stored in a non-transitory machine-readable medium.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIG. 8A is a schematic diagram of an inspection apparatus including a lock-in image detector according to another embodiment of the invention, adapted for dark-field imaging metrology with small targets;

FIG. 8B depicts a composite target and an outline of a measurement spot on a substrate, when measurements are being performed using the apparatus of FIG. 8A;

FIG. 8C depicts amplitude and phase images of the target of FIG. 8B obtained in the apparatus of FIG. 8;

DETAILED DESCRIPTION OF EXEMPLARY EMBODIMENTS

Figure 1:
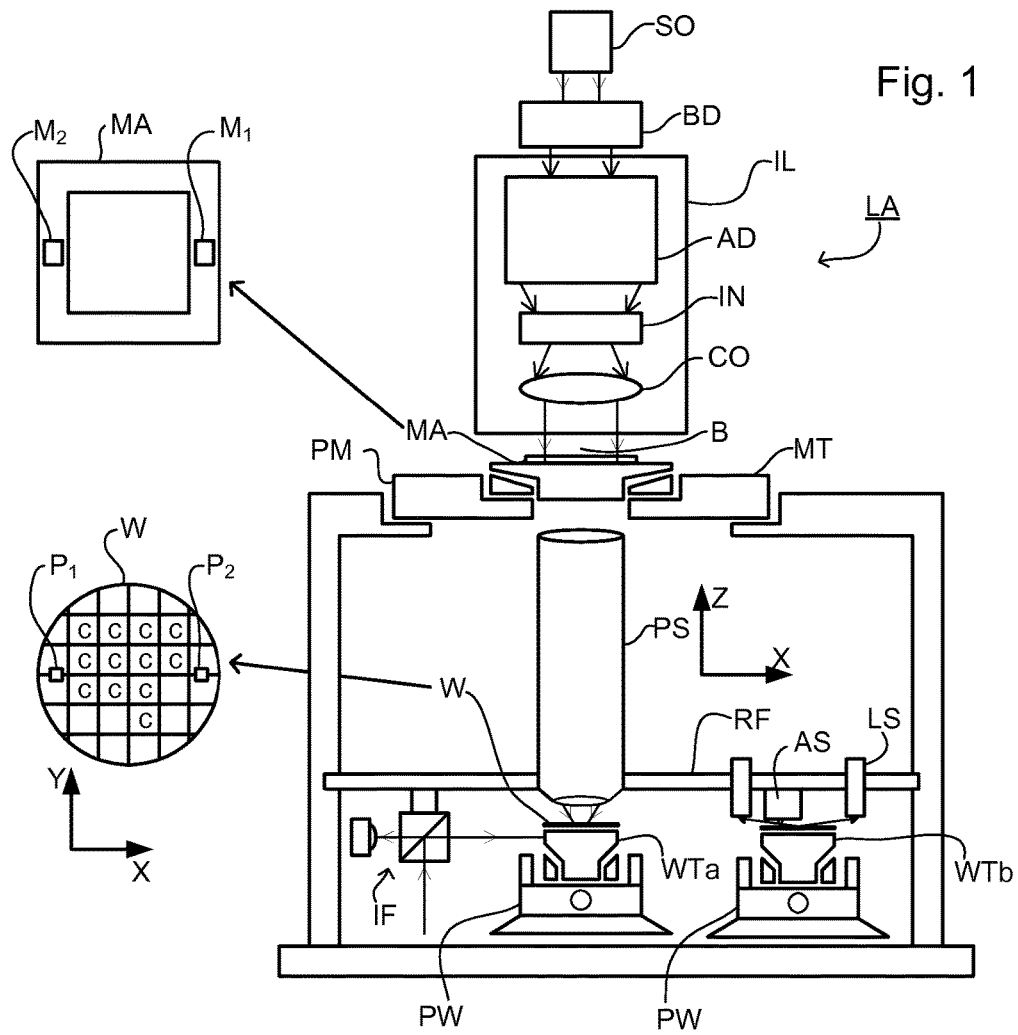
FIG. 1 depicts a lithographic apparatus.

FIG. 1 schematically depicts a lithographic apparatus. The apparatus comprises:
- an illumination system (illuminator) IL configured to condition a radiation beam B (e.g. UV radiation or DUV radiation).
- a support structure (e.g. a mask table) MT constructed to support a patterning device (e.g. a mask) MA and connected to a first positioner PM configured to accurately position the patterning device in accordance with certain parameters;
- a substrate table (e.g. a wafer table) WT constructed to hold a substrate (e.g. a resist-coated wafer) W and connected to a second positioner PW configured to accurately position the substrate in accordance with certain parameters; and
- a projection system (e.g. a refractive projection lens system) PL configured to project a pattern imparted to the radiation beam B by patterning device MA onto a target portion C (e.g. comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the mask MA with respect to the path of the radiation beam B, e.g. after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in a step mode or a scan mode. In step mode, the maximum size of the exposure field limits the size of the target portion C imaged in a single static exposure. In scan mode, the mask table MT and the substrate table WT are scanned synchronously while a pattern imparted to the radiation beam is projected onto a target portion C (i.e. a single dynamic exposure). The speed and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
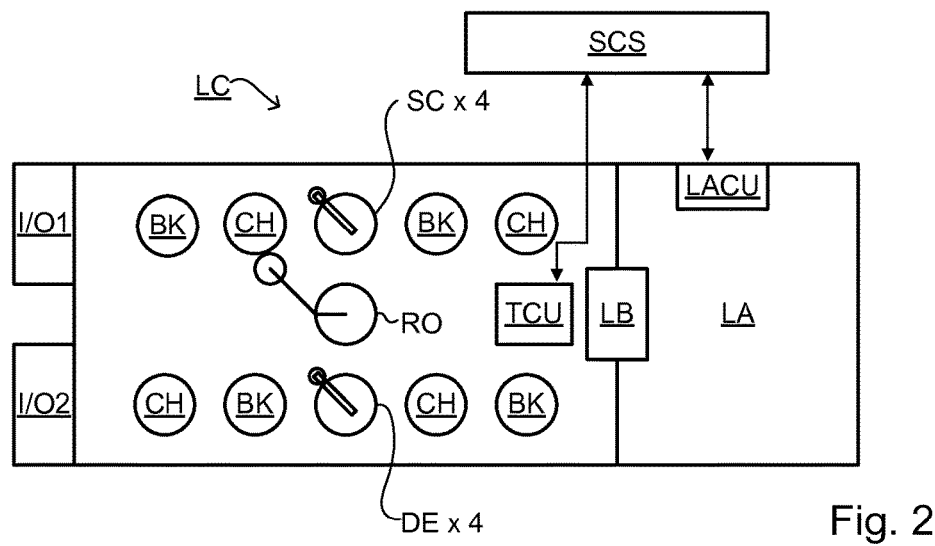
FIG. 2 depicts a lithographic cell or cluster.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer.

An inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Heterodyne Interferometric System for Scatterometry Based Metrology

Disclosed herein are modified inspection apparatuses and associated methods in which a lock-in image detector is used to perform scatterometry and/or dark-field imaging using a heterodyne interferometric technique. The modified apparatus provides measurements of the full-field diffraction pattern of a scattering target, including amplitude and phase instead of only intensity measurements. Target shape information can be obtained for parameters such as CD (critical dimension), and the apparatuses can also be used to obtain phase information to improve measurements of overlay, focus or dose.

Note that like reference numerals refer to like components throughout the figures.

Figure 3A:
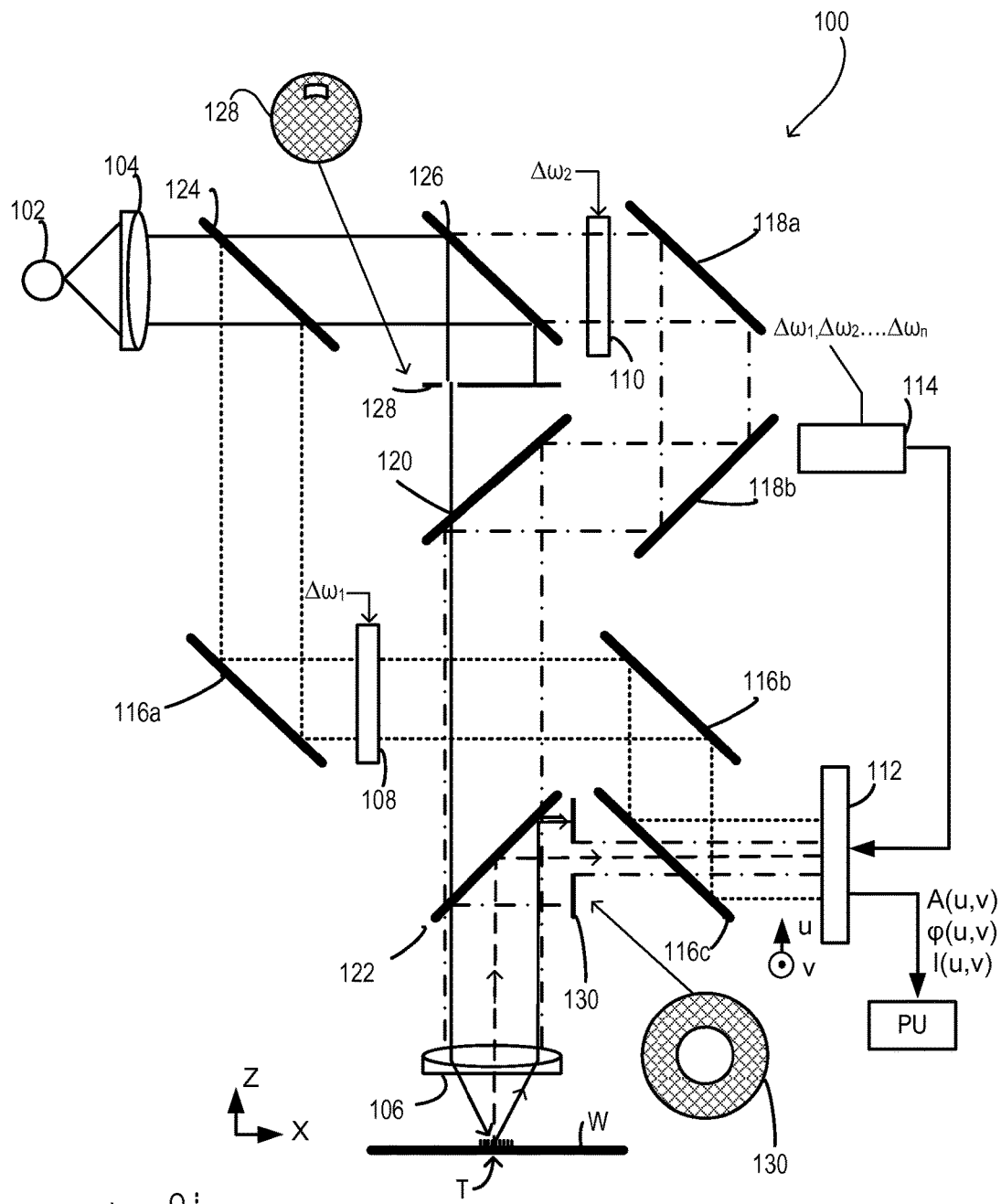
FIG. 3A is a schematic diagram of an inspection apparatus including a lock-in image detector according to an embodiment of the invention, with FIG. 3B a detail of incident and diffracted rays for a given direction of illumination.

FIG. 3A depicts in a simplified form an inspection apparatus 100 implementing a heterodyne interferometric technique. A grating target T and diffracted rays are illustrated in more detail in FIG. 3B. Apparatus 100 comprises a radiation source 102 and associated lens 104, an objective lens 106 facing a target T, a first frequency shifter 108, a second frequency shifter 110 and a lock-in image detector 112. These components are arranged in an optical system which defines effectively four beam paths. Rays following each of these paths are indicated in different line styles in FIG. 3A. As in a known apparatus, there is an illumination path for illuminating the target (solid ray lines) and a collection path for collecting diffracted radiation and delivering to the detector 112 (dashed ray lines). Additionally, there are provided in this apparatus a first reference path (dotted lines) that includes first frequency shifter 108 and a second reference path (dash-dot lines) that includes second frequency shifter 110. A frequency source 114 provides reference frequencies to the frequency shifters 108 and 110, as well as to the lock-in image detector 112. A processing unit PU receives image data from the lock-in image detector 112.

Image detector 112 in this example lies in a plane that is conjugate with a pupil plane of objective lens 106. In such a plane, one finds a portion of the diffraction spectrum of the target T. In other examples, to be described below, a lock-in image detector 112 lies in the plane of an image of the target T. In the present description, axes u and v are defined to refer to positions in a plane conjugate with the pupil plane, while axes x and y are defined to refer to positions in an image plane. As in the known apparatus, lock-in image detector 112 can deliver intensity values I(u,v) for any position in the pupil plane. Additionally, however, the provision of the frequency-shifted reference beam and a suitable reference frequency for the lock-in detector, means that the image detector in this example can provide separately amplitude values A(u,v) and phase values ϕ(u,v) for each position.

The mentioned beam paths can be implemented in many different layouts, and a particular configuration of mirrors 116a,b,c, 118a,b, 120, 122 and beam splitters (BS) 124, 126 is shown schematically here, only for illustration of the principles of the design. Not shown in the drawing are numerous components that would be included in a practical system, including for example lenses or other focusing elements. These can be adapted readily from the known apparatus and do not need to be described in detail. Additional beam paths for different functions (for example focusing, or different types of measurement) can also be provided.

Radiation source 102 may be a monochromatic coherent light source (e.g. a narrow linewidth laser). By using a coherent light source, the apparatus becomes less sensitive to differences in the optical path length and interferometric measurements become feasible. An incoherent light source (and additional components such as for example optical filters) could be used in the optical arrangement of FIG. 3, provided that the path length differences are negligible.

In the illumination path, a desired illumination profile may be defined. As a simple implementation of this, an aperture plate 128 of suitable form is placed between beam splitter 126 and mirror 120. As the aperture plate defines a spatial intensity distribution in a plane that is conjugate with a pupil plane of objective lens 106, the effect is to select the range of angles at which the illuminating radiation impinges on the substrate. In the example illustrated, aperture plate 128 has a given form to select an off-axis illumination mode. Other modes of illumination are possible by using different apertures. The rest of the pupil plane is desirably dark as any unnecessary light outside the desired illumination mode will interfere with the desired measurement signals.

Figure 3B:
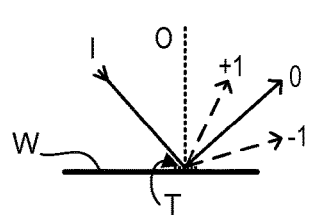

As shown in FIG. 3B, grating target T is placed with substrate W normal to the optical axis O of objective lens 106. A ray of illumination I impinging on target T from an angle off the axis O gives rise to a zeroth order ray (line 0) and two first order rays (lines +1 and −1). It should be remembered that with an overfilled small target grating, these rays are just one of many parallel rays covering the area of the substrate including metrology target T and other features. Where a composite grating target is provided, each individual grating within the target will give rise to its own diffraction spectrum. Since the aperture in plate 128 has a finite width (necessary to admit a useful quantity of light), the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the grating pitches and illumination angles can be designed or adjusted so that the first order rays entering the objective lens are closely aligned with the central optical axis. The +1 order rays illustrated in FIG. 3B is shown somewhat off axis, purely to enable it to be more easily distinguished in the diagram.

A field stop 130 may be provided between mirrors 122 and 116c. Field stop 130 in this example functions to block the zeroth order diffracted beam. It is located in a plane conjugate with a back pupil plane of objective lens 106, in the collection path, which may be referred to hereafter as a "collection pupil" or "detection pupil". The diffraction spectrum is then detected in a dark-field mode (not to be confused with a dark-field imaging mode, described in other examples).

The particular forms of aperture plate 128 and field stop 130 shown in FIG. 3 are purely examples. In other examples, on-axis illumination of the targets is used and an aperture stop with an off-axis aperture is used to pass substantially only one first order of diffracted light to the sensor. In yet other examples, 2nd, 3rd and higher order beams (not shown in FIG. 3) can be used in measurements, instead of or in addition to the first order beams. In order to make the illumination adaptable to these different types of measurement, the aperture plate 128 may comprise a number of aperture patterns formed around a disc, which rotates to bring a desired pattern into place. Alternatively or in addition, a set of plates 128 could be provided and swapped, to achieve the same effect. A programmable illumination device such as a deformable mirror array or transmissive spatial light modulator can be used also. Moving mirrors or prisms can be used as another way to adjust the illumination mode.

As mentioned, detector 112 is in the present apparatus a phase sensitive lock-in image detector. Lock-in detection is known generally as a technique that can perform narrowband (thus low noise) detection by 'tagging' part of the signal that contains information. The signal of interest is tagged by modulating the signal at a chosen frequency $\omega_D$, for example, away from noise frequency. A lock-in sensor is locked at the chosen frequency $\omega_D$ to record the signal of interest and to ignore other signals, or noise. In the present apparatus, a phase sensitive lock-in image detector comprising a two-dimensional array of pixels is used, each pixel providing a lock-in sensor function. A relative frequency shift is applied to the radiation in the diffracted beam and a reference beam. A beat frequency between these beam frequencies is used as the lock-in frequency for the lock-in image detector. In this way, the apparatus can be used to perform heterodyne interferometry to obtain the amplitude and phase information.

Figure 4:
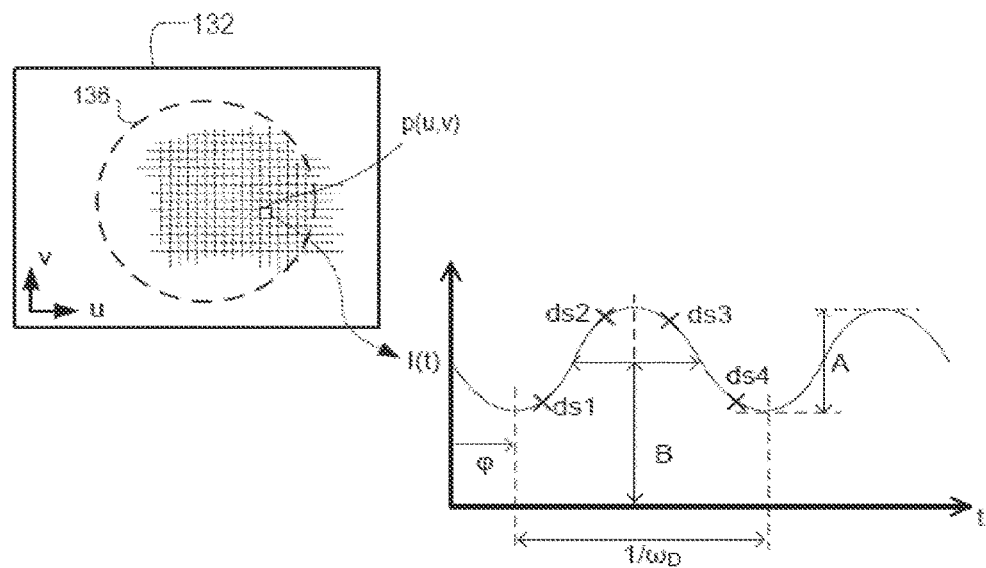
FIG. 4 illustrates the principle of operation of the lock-in image detector in the apparatus of FIG. 3A.

FIG. 4 illustrates the principle of operation of the lock-in image detector 112 locked at a frequency $\omega_D$. As in the known apparatus, an image sensor 132 comprises a two-dimensional array of light-detecting pixels. The axes of the array are labeled u and v, with p(x,y) representing a pixel at a position (u,v) of the sensor. A circle 136 represents the pupil of the collection optical path, where (in the example of FIG. 3) the diffraction spectrum of the target T will be found.

The graph in FIG. 4 shows the temporal evolution of an illumination intensity I(t) recorded at pixel p(u,v). A conventional image detector would simply integrate this intensity for an exposure interval, and output a single intensity per pixel. In the lock-in image detector, however, the radiation at each pixel p(u,v) is sampled separately multiple times (ds1, ds2, ds3, ds4) at intervals throughout a period of the reference frequency ($1/\omega_D$). For the present example, it is assume that there are four sampling points per period, separated by 90°. Assuming that the intensity waveform I(t) contains a sinusoidal component synchronized with reference frequency $\omega_D$, this will give different values for the samples ds1-ds4 as illustrated. The samples ds1-ds4 may be integrated over several periods to obtain signals s1, s2, s3, s4. In this way, frequency components of the intensity waveform that are not synchronized with the reference frequency will be averaged out and the four values s1-s4 allow calculation of the phase and amplitude of the synchronized component. For example, the amplitude A, phase $\phi$ and dc offset B of the synchronized component can be calculated by the formulae:

$$A = \frac{\sqrt{(s2-s4)^2 + (s1-s3)^2}}{2}$$

$$\varphi = \arctan\frac{(s1-s3)}{(s2-s4)}, \text{ and}$$

$$B = \sum_{i=1}^{4} s_i/4.$$

Intensity of this component can be calculated as $I=A^2$.

The image sensor 132 may for example be an adapted CMOS image sensor. Note that single-photon avalanche diodes (SPADs), CCDs or any other suitable sensors may also be used as detectors. Readers skilled in the art will be able to adapt known lock-in methods and/or phase-sensitive detection methods to detect amplitude and phase images as described herein. While FIG. 3 shows the amplitude and phase values emerging from the lock-in image detector 112, it is a matter of design choice whether these values are calculated in the detector itself, or within the processing unit PU. In practice, it may be convenient if processing unit PU receives the raw samples ds1-ds4, or the integrated values s1-s4 from the lock-in image detector, and then performs the calculations of amplitude, phase, intensity as desired. Note also that amplitude and phase information need not be expressed in the form of values A and $\phi$. The amplitude and phase information for each pixel may be represented by a pair of component vectors U and V. The conversion between these forms of expression is easily done by expressing the amplitude and phase as complex number according to the well-known relation:

$$U+iV=Ae^{i\phi}$$

Returning to FIG. 3, the apparatus 100 comprises frequency shifters 108,110 to enable lock-in detection for the heterodyne interferometric technique, and for an improved normalization function. The number of frequency shifters and the frequency modulation technique may be chosen to match the application requirements. A frequency shifter may be for example an electro-optic modulator, a fiber modulator, a magneto-optical modulator, a modulator based on Zeeman Effect and/or preferably an acousto-optic modulator. For the sake of example, frequency shifters 108,110 may be acousto-optic modulators (AOMs).

As known by persons skilled in the art, an AOM operates by setting up acoustic waves in a crystal. These waves form a kind of moving Bragg grating within the crystal, with a speed of movement determined by the driving frequency. Incident light (at a frequency $\omega$) focused onto the AOM in the Bragg regime (to satisfy the Bragg condition), is mainly diffracted into a first order output beam and a zero order output beam, separated by twice the acoustic Bragg angle. The motion of the "grating" within the AOM also causes the frequency of the first order output beam to be frequency-shifted by $\omega+m\Delta\omega$, with m=1 corresponding to the first order diffraction and $\Delta\omega$ the modulation frequency. For the first order diffracted light, the frequency shift of the frequency is equal to the modulation frequency of the AOM. The frequency shifters (AOMs) 108, 110 may be driven by frequency source 114 at different modulation frequencies, such that for example $\Delta\omega_1$ may be 30 kHz $\Delta\omega_2$ may be 100 kHz. Such a small shift in frequency has no impact on scattering/diffraction effects. The exact frequency and phase is unimportant, so long as the lock-in image detector receives its reference signal from the same frequency source as the AOM.

Using the frequency shift $\Delta\omega_1$, inspection apparatus 100 implements a kind of heterodyne interferometric technique and thus allows measurement of amplitude and phase of the diffraction pattern at the detector 112, rather than only intensity.

Previous approaches to obtain phase information for this purpose are described in, for example, "Phase retrieval between overlapping orders in coherent Fourier scatterometry using scanning" N. Kumar et al. Journal of the European Optical Society—Rapid publications, Europe, v 8, July 2013, ISSN 1990-2573. The Kumar reference includes work described in the patent application US2012243004A1, mentioned above. Arrangements based on heterodyne interferometry are, for example, disclosed in G. E. Sommargren Applied Optics, Vol. 20, Issue 4, pp. 610-618 (1981) and M. Pitter et at Optics Letters, Vol. 29, No. 11, Jun. 1 (2004). A heterodyne scatterometer for detecting and analyzing wafer surface defects is disclosed in U.S. Pat. No. 5,923,423 A. As mentioned already, these known approaches generally require multiple measurements and scanning movements to access the phase information, and so are not so well suited to inspection in high-volume manufacturing. Phase sensitive detection techniques and examples of applications of phase sensitive imaging are disclosed in "CMOS cameras for phase sensitive imaging" by M. Pitter et al. Institute of Biophysics, Imaging and Optical Science University of Nottingham, UK, published at http://www.physics.ox.ac.uk/lcfi/FastImSem/Pitter.pdf. According to the present application, a lock-in image detector similar to that disclosed by Pitter is applied to scatterometry and/or diffraction based metrology for measurement of parameters of a lithographic process.

In the inspection apparatus 100 of FIG. 3, the radiation beam emitted by radiation source 102 is split in three beams (an illumination beam, a first reference beam and a second reference beam) by beam splitters 124 and 126 and each of the beams follows a specific optical path.

The illumination path and collection paths followed by the illumination beam are similar to illumination and collection paths of the known scatterometers. In the present example, however, radiation source 102 emits monochromatic radiation of frequency $\omega$. The illumination beam of frequency $\omega$ is given a desired profile by aperture 128 and focused onto substrate W via objective lens 106. Objective lens 106 has a high numerical aperture (NA), preferably at least 0.9 and more preferably at least 0.95. Using immersion techniques the scatterometer may even have lenses with numerical apertures over 1. The incident radiation (still at frequency $\omega$) is diffracted by the target on substrate W into a diffraction spectrum. At least the $0^{th}$ order and optionally higher order beams are collected by objective lens 106 and directed back to mirror 122. Mirror 122 directs the scattered/diffracted radiation via field stop 130 and mirror 116c to lock-in image detector 112. The signals detected by detector 112 are output to processor and controller PU, and used in calculations which will depend on the particular type of measurements being performed.

In order to make the collection pupil adaptable to different types of measurement, the field stop 130 may comprise a number of aperture patterns formed around a disc, which rotates to bring a desired pattern into place. Alternatively or in addition, a set of field stops 130 could be provided and swapped, to achieve the same effect. A programmable field stop device such as a deformable mirror array or transmissive spatial light modulator can be used also. Moving mirrors or prisms can be used as another way to adjust the collection/imaging mode. References to field stop in this description and claims should be interpreted as including any device that allows selection of a desired portion of the diffraction spectrum of the target to be transmitted in the collection path.

Recall that detector 112 in this example 're-images' the back pupil plane of the objective lens. The pupil plane is the plane in which the radial position of radiation defines the angle of incidence and the angular position defines azimuth angle of the radiation. Detector 112 may also be located in the back-projected pupil plane, which is at the focal length of the lens system 106. Only selected portions of the diffraction spectrum are incident on the detector. Which portions these are depends on: (i) the selected direction(s) of illumination; (ii) the angular spread of the diffraction orders which depends on the periodicity of the target grating in relation to the illumination wavelength $\lambda$; and (iii) the selection of parts of the spectrum by field stop 130. For diffraction-based metrology, we suppose that at least one of the higher orders are included in the selected portion (for example $+1^{st}$ and/or $-1^{st}$ order). Scatterometry is however possible with only the $0^{th}$ order included, and embodiments with such an arrangement are not excluded. Throughout this description, from FIG. 3 onward, the term 'diffraction pattern' or 'diffraction spectrum' will be used for convenience. Unless the context otherwise requires, no specific portion of the diffraction spectrum is intended to be included or excluded on the assumption that an inspection apparatus based on heterodyne interferometric technique of this disclosure is used. The skilled person can readily adapt the teaching to different types of scatterometer, or even other types of measurement instrument.

To implement an heterodyne interferometric technique, the first reference beam, following the first reference path, is directed to frequency shifter (AOM) 108 via mirror 116a. The frequency of the first reference beam is shifted by the AOM to a frequency $\omega+\Delta\omega_1$ and then the frequency-shifted first reference beam (i.e. the first order diffracted beam) is directed to detector 112 by mirrors 116b,c.

An additional second reference beam, following the second reference path, is directed to frequency shifter (AOM) 110 via beam splitters 124 and 126. The frequency of the second reference beam is shifted by the AOM to a (different) frequency $\omega+\Delta\omega_2$. The frequency-shifted second reference beam (i.e. the first order diffracted beam) is then directed to mirror 120 by mirrors 118a,b. From mirror 120, the frequency-shifted second reference beam follows the same optical path as the illumination beam. The frequency-shifted second reference beam at a frequency $\omega+\Delta\omega_2$ is thus focused onto substrate W via a microscope objective lens 106, reflected back and directed to detector 112. The second reference beam differs from the illumination beam in that it has no specific illumination profile.

In this configuration, the diffracted beam at frequency $\omega$, the first reference beam at a frequency $\omega+\Delta\omega_1$ and the second reference beam at a frequency $\omega+\Delta\omega_2$ overlap at detector 112, creating interference patterns at the detector.

Because of the frequency shifts, these interfering beams set up characteristic and the "beat" frequencies. The three interfering beams generate signals having the following four beat frequencies: $\Delta\omega_1$, $\Delta\omega_2$, $\Delta\omega_2-\Delta\omega_1$, $\Delta\omega_2+\Delta\omega_1$. These can be separately detected using the lock-in image detector, using the principles described already with reference to FIG. 4.

The information associated to the measured scattered signal and encoded in the signals generated by interfering signals (By setting the lock-in reference frequency $\omega_D$ to a selected one of $\Delta\omega_1$, $\Delta\omega_2$, or $\Delta\omega_2-\Delta\omega_1$ any of the following information signals may be retrieved independently as desired:

From the signal locked at frequency $\Delta\omega_1$: Amplitude, phase and intensity of the measurement signal (that is the selected portion of the diffraction spectrum of target T) at each pixel p(u,v), relative to the first reference beam. Assuming that the reference beam has a constant or at least well-defined phase across the detection pupil, then the phase of the signal at this beat frequency represents directly the phase of the optical signal diffracted from the target T. This phase can be detected independently at each pixel.

From the signal locked at frequency $\Delta\omega_2$: Amplitude, phase and intensity of the measurement signal relative to the second reference beam. In our application, this signal is not necessarily useful for the far-field diffraction measurement. However, it may be used for other purposes including for example focus estimation, based on the teaching of Kumar et al, cited above. The content of the Kumar et al reference is hereby incorporated herein by reference, for this teaching.

From the signal locked at frequency $\Delta\omega_2-\Delta\omega_1$: A reference signal can be obtained and used for intensity normalization.

The signal at $\Delta\omega_2+\Delta\omega_1$ may be neglected.

In principle, a single lock-in image detector can retrieve only one of these signals at any given time. To retrieve more than one of these information signals, detector 112 may be sequentially frequency-locked at each of the frequency of interest to record the signals of interest one after another. Alternatively, several detectors may also be employed in parallel, to obtain the different information signals simultaneously. Alternatively, more than four sampling and integration circuits implemented within a single lock-in image detector 112, in order to distinguish multiple frequency components simultaneously.

Having introduced the form and function of the apparatus in detail, we will now describe practical applications of the apparatus and the various information signals, and alternative examples of apparatus and method will now be described.

Application to Intensity Normalization in Optical Metrology

Referring to the last of the information signals mentioned above, processing unit PU uses intensity normalization information to compensate for variations in the intensity of the illumination source 102, so that they do not become mistaken for variations in a property of the target. Compared with the path followed by a normalization reference beam in the known scatterometers, the second reference beam in the present example follows a path through the optical system that is almost identical to the path followed by the illumination and collection paths used in the real measurements. Therefore this signal allows a more accurate normalization of measurement results, By applying the specific frequency shift and lock-in detection, it is ensured that the second reference beam can follow the same path as the illumination and detection of diffracted radiation, without influencing the first information signal. Conversely, though they follow the same path and use the same detector (unlike the known apparatus), the diffracted signal does not influence measurement of the intensity normalization.

An intensity image I(u,v) may be sufficient for the purpose of normalization, though of course phase information can be retrieved if desired.

Application to Diffraction-Based Metrology/Scatterometry

As is well known, the methods in which scatterometry and diffraction-based metrology can be performed are numerous, and only a few examples will be described here, to illustrate the application of a generally-applicable new technique. Common to the examples disclosed hereunder is that the diffracted radiation is captured with phase information. In other words, the image captured has pixel values that can be regarded as complex numbers or vectors rather than a simple scalar value per pixel. As the vectors represent phase information of a periodic function, they may also be referred to as 'phasors'.

Application Examples with Pupil Image Detection

Figure 5A:
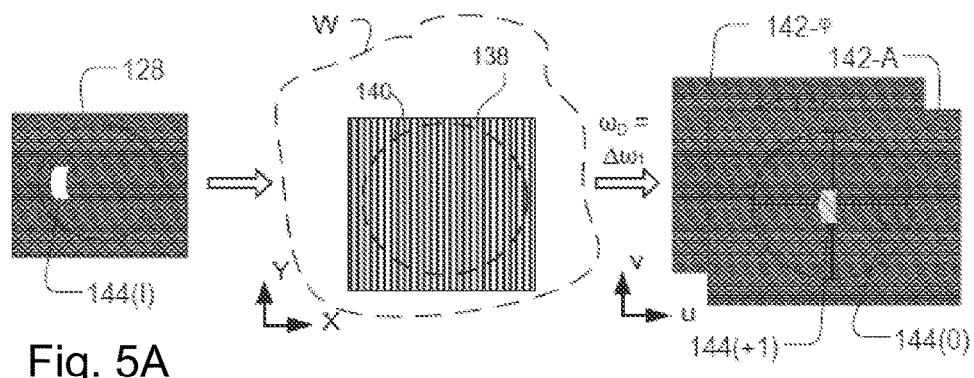
FIGS. 5A and 5B illustrate the obtaining of amplitude and phase components of diffraction patterns, using the apparatus of FIG. 3A in different illumination modes.
Figure 5B:
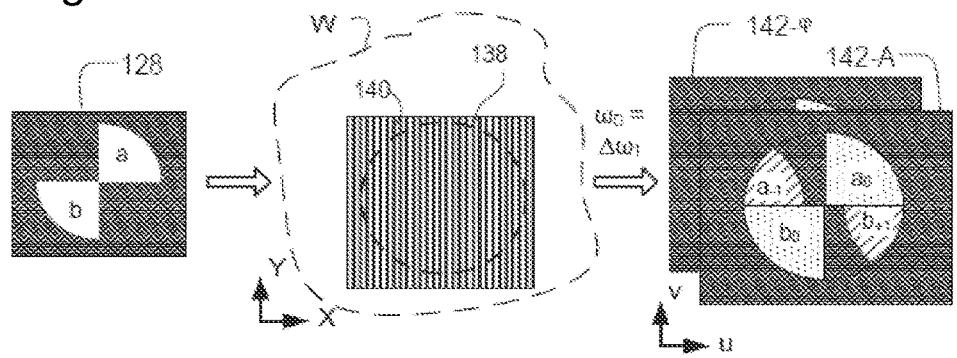

FIGS. 5A and 5B show examples of diffraction pattern images obtained corresponding to two illumination modes that may be formed on and detected by detector 112. At the center of each part of the figure, there is shown target grating 138 that is in this example underfilled by an illumination spot 140 formed by the illumination beam of the metrology apparatus. Not shown in the drawing, this grating 138 may be part of a larger set of gratings forming component gratings of a composite target. The grating is one-dimensional with periodicity in the X direction. Y-direction gratings will also be provided, and/or gratings with oblique lines or two-dimensional periodicity.

The examples of FIGS. 5A and 5B depict operation the case where lock-in detector 112 is locked at a frequency for example equal to $\Delta\omega_1$. In this case, as explained above, detector 112 would only "see" the information signal at a frequency $\Delta\omega_1$ generated by the interference between the beam at a frequency $\omega$ that has been diffracted by target T and the first reference beam at a frequency $\omega+\Delta\omega_1$ that has come substantially directly from the illumination source. The illumination profile provided by a given form of aperture plate 128 is illustrated at the left side in each figure. Detector 112 allows measurements of phase 9 and amplitude A of the optical field and (if desired) the intensity I of the detected signal. To illustrate the separation of amplitude and phase associated by detector 112, two separate detected images are represented at the right hand side in each part of the figure. Images 142-A and 142-φ capture amplitude and phase of the detected signal, respectively. Showing the complex pixel values as two different images is purely illustrative. They can be processed as two separate images or treated as a single image with complex pixel values (similar to different color channels in a digital color photograph). As mentioned above, an intensity image can also be calculated but this is not shown in the drawing. Also, as mentioned above, the amplitude and phase components can be expressed indirectly through a pair of orthogonal component vectors of an electric field, $E_x$ and $E_y$. The expression of the values in terms of A and φ is a matter of choice. Moreover, there is no reason why intensity and phase (I and φ) should not be used instead of amplitude and phase.

In FIG. 5A, the illumination profile defines a single patch of illumination 144(I) away from the optical axis. This is the example illustrated in FIG. 3. Due to the action of field stop 130, only the +1 order diffraction signal is visible, labeled 144(+1). Other diffraction orders (including the $0^{th}$ order indicated in dotted outline at 144(0)) are blocked by field stop 130, or do not even enter the objective lens (e.g. the −1 order seen in FIG. 3B, and orders higher than first order.) This use of off-axis illumination pattern can be exploited to obtain clear first order signals from a diffraction grating (overlay target) having a pitch which is half the minimum pitch that could be imaged if a conventional, circularly-symmetric illumination aperture were used. However, the −1 order diffraction signal normally needs to be obtained for comparison. This arrangement therefore requires measuring the target twice under different conditions, while either rotating the target or changing the illumination mode or imaging mode to obtain separately the $-1^{st}$ and the $+1^{st}$ diffraction orders.

In the example of FIG. 5B, the field stop 130 is removed from inspection apparatus 100 of FIG. 3 and the aperture stop 128 of FIG. 5A is replaced by the segmented aperture stop 128 of FIG. 5B. This type of aperture has two illuminated quadrants labeled a and b that are diametrically opposite one another in the illumination pupil, with dark quadrants in between. Therefore, the zero order reflections labeled $a_0$ and $b_0$ and first order diffraction signals labeled $a_{-1}$, $a_{+1}$, $b_{-1}$ and $b_{+1}$ are visible in the detected images 142-A and 142-φ. Because other quadrants of the illumination aperture are dark, and more generally because the illumination pattern has 180° rotational symmetry, the diffraction orders $a_{-1}$ and $b_{+1}$ are "free" in the detected images, meaning that they do not overlap with the zero order or higher order signals from other parts of the illumination aperture. This property of the segmented illumination pattern can be exploited to obtain clear first order signals from a diffraction grating (overlay target) having a pitch which is half the minimum pitch that could be imaged if a conventional, circularly-symmetric illumination aperture were used. At the same time, two opposite first order signals can be extracted from different regions of the same (complex) image, so that it is not necessary to make separate measurements. This diffraction pattern and the manner in which it can be exploited for scatterometry, are described in the known application US 20100201963, with further examples below.

Application Example of a Target Reconstruction Process

Using an inspection apparatus described above in combination with modeling of a target structure such as the target T and its diffraction properties, measurement of the shape and other parameters of the target can be performed in a number of ways. In an example of such a process, represented by FIG. 6, a diffraction pattern based on a first estimate of the target structure (a first candidate structure) is calculated and compared with the observed diffraction pattern. Parameters of the model are then varied systematically and the diffraction re-calculated in a series of iterations, to generate new candidate structures and so arrive at a best fit. Whereas, with the conventional scatterometer, one can compare only intensities between the modeled diffraction pattern and the observed one, with the apparatus of FIG. 3 amplitude and phase (or intensity and phase) can be compared. In the following discussion, amplitude and phase (or intensity and phase) will be abbreviated to "amplitude/intensity and phase". This phrase should also be understood to encompass alternative forms of expression, as discussed above.

Figure 6:
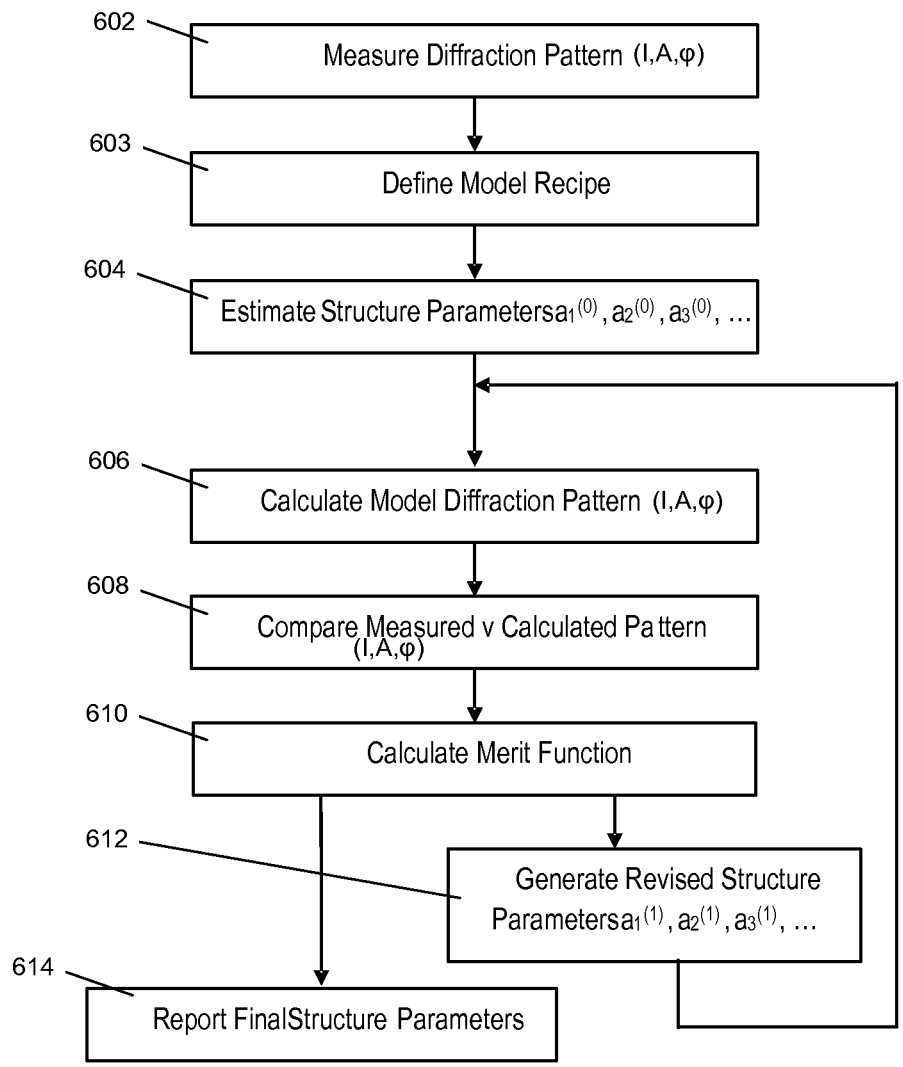
FIG. 6 depicts an example process for reconstruction of a structure from diffraction patterns of the type shown in FIG. 5A or 5B

Referring to FIG. 6 in more detail, the target will be assumed for this description to be periodic in only 1 direction (1-D structure). In practice it may be periodic in 2 directions (2-dimensional structure), and the processing will be adapted accordingly.

602: The far-field diffraction pattern of the target, including phase information, is measured using a scatterometer such as those described above. This measured diffraction pattern is forwarded to a calculation system such as a computer. The calculation system may be the processing unit PU referred to above, or it may be a separate apparatus. The diffracted signal intensity (I) and/or amplitude (A) and phase (ϕ) of the associated optical field are thus retrieved.

603: A 'model recipe' is established which defines a parameterized model of the target structure in terms of a number of parameters a, ($a_1$, $a_2$, $a_3$ and so on). These parameters may represent for example, in a 1-D periodic structure, the angle of a side wall, the height or depth of a feature, the width of the feature. Properties of the target material and underlying layers are also represented by parameters such as refractive index (at a particular wavelength present in the scatterometry radiation beam). Importantly, while a target structure may be defined by dozens of parameters describing its shape and material properties, the model recipe will define many of these to have fixed values, while others are to be variable or 'floating' parameters for the purpose of the following process steps. Prior applications disclose processes by which the choice between fixed and floating parameters can be made. Moreover, such prior applications introduce ways in which parameters can be permitted to vary without being fully independent floating parameters. For the purposes of describing FIG. 6, only the variable parameters are considered as parameters $p_i$.

604: A model target structure is estimated by setting initial values $a_i^{(0)}$ for the floating parameters (i.e. $a_1^{(0)}$, $a_2^{(0)}$, $a_3^{(0)}$ and so on). Each floating parameter will be generated within certain predetermined ranges, as defined in the recipe.

606: The parameters representing the estimated target structure, including shape together with the optical properties of the different elements of the model, are used to calculate the scattering properties, for example using a rigorous optical diffraction method such as RCWA or any other solver of Maxwell equations. This gives an estimated or model diffraction pattern of the estimated target structure. Whereas in prior applications one would convert the modeled far field diffraction pattern to simple intensity values, the step 606 in the present application keeps separate values of amplitude/intensity and phase, or vectors $E_x$, $E_y$ to express amplitude/intensity and phase in whatever form is convenient.

608, 610: The measured diffraction pattern (amplitude/intensity and phase) and the model diffraction pattern are then compared and their similarities and differences are used to calculate a "merit function" for the model target structure. For this step, considering that the amplitude/intensity and phase obtained in steps 602 and 606 can be expressed in various ways, it will normally be convenient to choose the same form of expression for both steps. Otherwise, the comparison in step 608 may involve some pre-conversion.

612: Assuming that the merit function indicates that the model needs to be improved before it represents accurately the actual target structure, new parameters $a_1^{(1)}$, $a_2^{(1)}$, $a_3^{(1)}$, etc. are estimated and fed back iteratively into step 506. Steps 606-612 are repeated.

In order to assist the search, the calculations in step 606 may further generate partial derivatives of the merit function, indicating the sensitivity with which increasing or decreasing a parameter will increase or decrease the merit function, in this particular region in the parameter space. The calculation of merit functions and the use of derivatives is generally known in the art, and will not be described here in detail.

614: When the merit function indicates that this iterative process has converged on a solution with a desired accuracy, the currently estimated parameters are reported as the measurement of the actual target structure.

The computation time of this iterative process is largely determined by the forward diffraction model used, i.e. the calculation of the estimated model diffraction pattern using a rigorous optical diffraction theory from the estimated target structure. If more parameters are required, then there are more degrees of freedom. The calculation time increases in principle with the power of the number of degrees of freedom. The estimated or model diffraction pattern calculated at 606 can be expressed in various forms. Comparisons are simplified if the calculated pattern is expressed in the same form as the measured pattern generated in step 602. For example, a modeled pupil pattern can be compared easily with a pupil pattern measured by the apparatus of FIG. 3. Processes for determining structure parameters are further detailed, for example, in WO 2012126718.

The comparison of both amplitude/intensity and phase can be expected to improve the robustness of the iterative process, in that there is more information by which the effects of different model parameters can be distinguished. The improved performance may be realized in terms of reduced computational burden (for example fewer iterations and/or fewer variable parameters required) and/or in terms of greater accuracy of the final result. The prior application US2012243004A1 mentioned above provides more detailed illustrations of the use of phase information in target reconstruction.

Another method, not illustrated by a flowchart, uses a library of pre-calculated diffraction patterns, instead of calculating the model at the time of making each measurement. Measurements of the parameters of interest are obtained by searching in the library for a pattern which best matches the observed diffraction pattern, and then looking up the shape and other parameter values that were used to generate the library pattern. The library searching can be made more discriminating by using both the amplitude/intensity image and the phase image as criteria for finding the best matching pattern in the library. Hybrid methods can also be implemented using a combination of searching in a library followed by iterative modification.

The measurements above are performed with the lock-in image detector 112 synchronized with the beat frequency $\Delta\omega_1$. Measurements for intensity normalization can be performed at convenient times during the process by setting the lock-in frequency to $\Delta\omega_2-\Delta\omega_1$, as described above. Alternatively, a separate detection branch with lock-in frequency $\Delta\omega_2-\Delta\omega_1$ can be operated in parallel with the measurements at $\Delta\omega_1$. Normalization can be applied to the measured diffraction pattern at an appropriate stage in the method of FIG. 6, that is at some time between steps 602 and 608. In examples where key parameters are extracted from the diffraction pattern for comparison with the model, normalization will typically be performed on the raw amplitude/intensity data, prior to extracting key parameters.

Application Example: Diffraction Based Overlay in the Pupil Plane

Figure 7A:
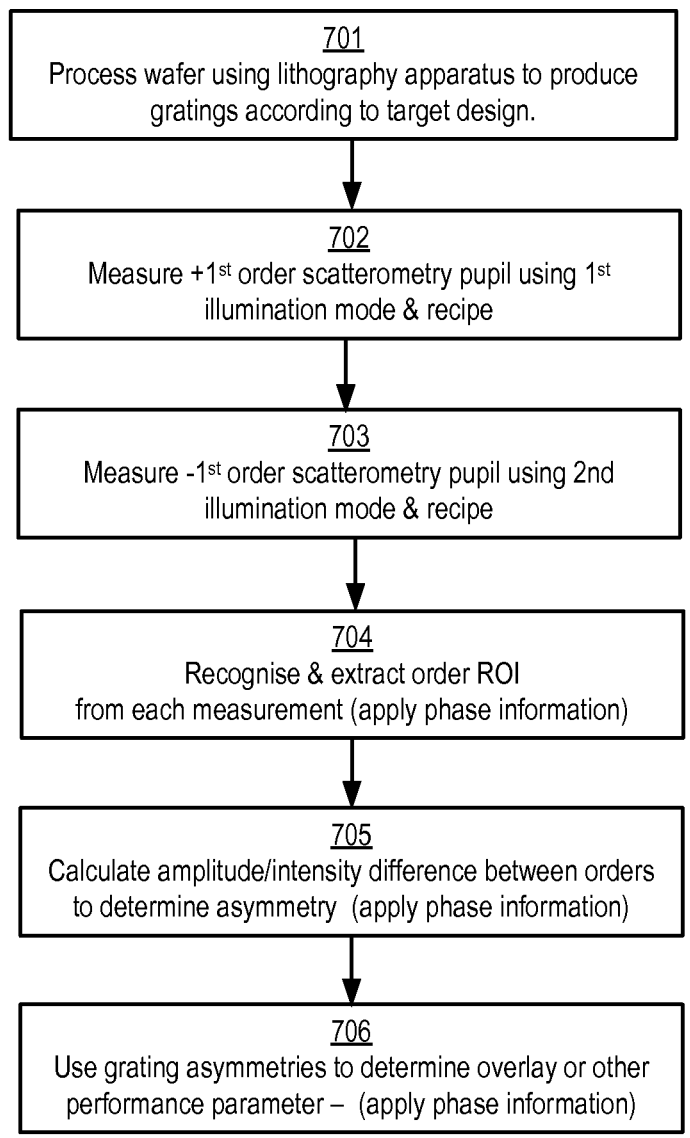
FIGS. 7A and 7B depict example processes for determining overlay or other performance parameters from diffraction spectra of the type shown in FIG. 5A or 5B, respectively.
Figure 7B:
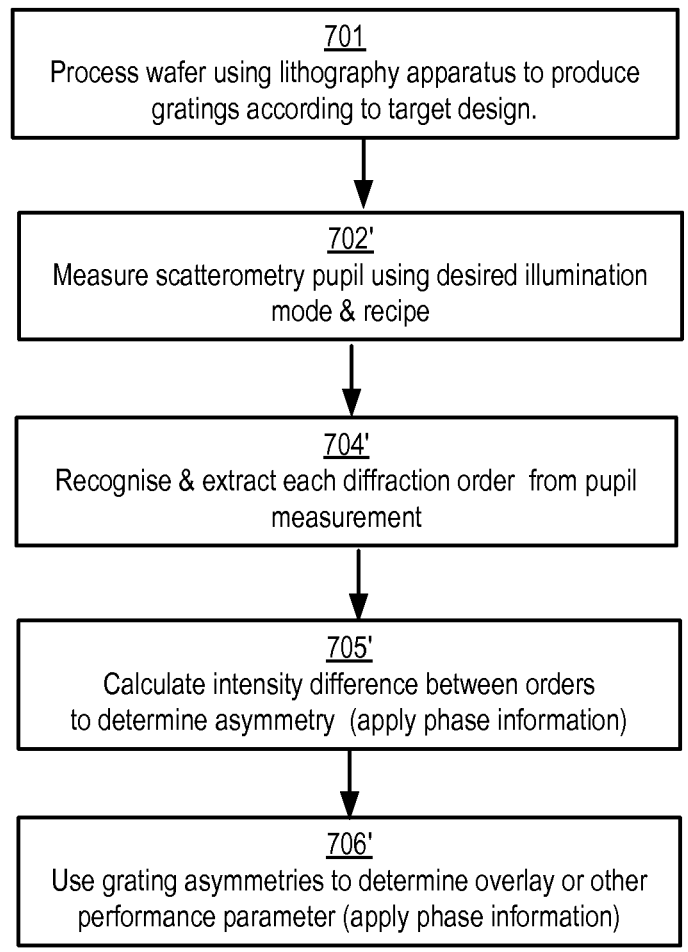

Referring to FIGS. 7A and 7B, other prior applications mentioned above disclose how various performance parameters of a lithographic process can be measured by simply observing asymmetries in diffraction patterns. Overlay measurements, for example, may be inferred from the diffraction patterns of FIG. 5A or 5B from the targets 138 measured by detector 112. The grating 138 in an overlay target comprises two gratings formed on top of one another in first and second layers on a substrate. Asymmetry can also be used with other specially formed targets to measure parameters other than overlay, for example to measure focus or dose performance of the lithographic process. These techniques involve fine features on one side or another of grating lines, in such a way that non-ideal focus or dose settings result in an asymmetric shape of each line. Another form of overlay is overlay between interleaved lines made by a multiple patterning process. The present techniques, described in the example of overlay metrology, can be adapted readily to all these types of metrology. An asymmetry signal for grating 138 (for example) may be obtained by comparing intensities of the +1 and −1 orders extracted from a pair of diffraction pattern images (as in FIG. 5A) or from different regions within the same diffraction pattern (FIG. 5B, captured using detector 112.

FIG. 7A shows an example process applicable in the situation depicted in FIG. 5A, where opposite portions of the diffraction spectrum (for example +1 order and −1 order) are recorded at detector 112 in two separate measurements. At step 701, the substrate, for example a semiconductor wafer, is processed through the lithographic cell of FIG. 2 one or more times, to create a structure including the overlay targets 138. At 702, using the metrology apparatus of FIG. 3 with the aperture plate 128 of FIG. 5A left hand side, the +1 order diffraction pattern of FIG. 5A right hand side is obtained. t 703 a −1 order diffraction pattern is obtained, by for example rotating the target or changing the illumination mode.

In step 704, a region of interest (ROI) is optionally identified within the diffraction patterns obtained at step S2 and S3, from which intensity levels will be measured. Whether this step is necessary depends whether the diffraction pattern might contain noise outside the region 144(+1) etc. where the selected diffraction orders are found.

Having identified the ROI for each diffraction order and measured its intensity, the asymmetry of the grating structure, and hence overlay error (or other parameter), can then be determined. This is done by the image processor and controller PU in step 705 comparing the amplitude/intensity values (and optionally phase) obtained for +1 and −1 orders for targets 138 to identify any difference in their intensity. The amplitude/intensity difference is calculated at step 705 to obtain a measurement of asymmetry for each grating. At step 706, from the asymmetry measurements and from knowledge of the overlay biases of the gratings, a processor calculates overlay error in the vicinity of the target T.

Now, while the measurement of asymmetry of the diffraction spectrum is a good way to measure overlay in a perfectly implemented process, in reality, other factors, such as process-induced asymmetry in top or bottom grating features may influence the results undesirably. Other variations in material and shape may likewise reduce the accuracy of the overlay measurement inferred from the asymmetry measurement. The availability of phase information in addition to amplitude/intensity information from the lock-in image detector 112 can be exploited to improve accuracy without the need to take further measurements. The phase images 142-ϕ of the two diffraction patterns can be compared in step 705 to obtain additional information on the type (cause) of the observed asymmetry. Alternatively or in addition, after comparing amplitudes or intensities in step 705, information from the phase image can be used to calculate a correction in the calculation of the parameter of interest performed at step 706. Alternatively or in addition, phase information can be applied to calculate corrections in the measured amplitudes or intensities prior to the comparing in step 705. As a particular application, phase information can be applied to calculate focus corrections for the captured images. These focus corrections can be applied for example to define more accurately the ROIs in step 704, or in another way to extract more accurately the desired diffraction orders.

FIG. 7B is very similar to FIG. 7A and is an example of an equivalent process, performed in the situation depicted in FIG. 5B. Recall that, using the metrology apparatus of FIG. 3 with for example the aperture plate 128 of FIG. 5B, both +1 and −1 diffraction orders are recorded in one measurement, but at different parts of the (complex) image. Therefore, steps 702 and 703 are replaced by a single step 702' in which both +1 and −1 diffraction orders are recorded simultaneously. Then, in step 704' two regions of interest (ROI) are carefully identified within the diffraction pattern obtained at step 702' to extract selected opposite portions of the diffraction spectrum (in this example the +1 and −1 diffraction orders), from which intensity levels (optionally phase) will be measured. Having identified the ROI for each diffraction order and measured its amplitude/intensity (optionally phase), the asymmetry of the grating structure, and hence the parameter of interest such as overlay error, can then be determined at steps 705' and 706'. Phase information can be used in steps 704', 705' and/or 706' to improve accuracy, as explained for FIG. 7A.

Application Examples: Dark Field Imaging Metrology

As mentioned in the introduction, another type of inspection apparatus for diffraction-based metrology employs dark-field imaging instead of pupil image detection. In practice, as shown in the referenced prior applications, optical systems for the dark-field imaging function and the pupil plane imaging can share many components, and both types of apparatus can usefully be combined in a single commercially available apparatus. The dark-field imaging function and pupil imaging function can be provided by splitting the beams into different branches, as illustrated in the prior applications. Alternatively, movable components may be provided to convert a single branch of the optical system into one form instead of the other. The examples below have just a dark-field imaging function, for simplicity. Again, the optical system in a real product would include many ancillary components such as lenses and polarizers. These are not shown in the drawings, for clarity.

FIG. 8A depicts an inspection apparatus 800 adapted to perform dark-field imaging and incorporating a lock-in image detector and frequency shifters, to implement a heterodyne interferometric technique. The optical arrangement is generally the same as the arrangement of FIG. 3, and the same reference numbers are used for equivalent components. Only the differences will be described here. The principal difference from the apparatus of FIG. 3 is in the provision of an imaging lens 802 (or lens system). The radiation scattered from target T and the reference beam are focused by optical system 802 to form an image of the target T on the substrate W on lock-in image detector 112. That is to say, the detector 112 now lies in a plane conjugate with the plane of the target, instead of a plane conjugate with a pupil plane of objective lens 106. Coordinates in this plane are labeled x and y, rather than u and v. As is known from the references, adopting the dark-field imaging mode of operation allows the use of smaller targets, and allows measurements from multiple small targets to be taken simultaneously. This can bring benefits in that it uses less space on the substrate, and in that a high measurement throughput can be maintained, for metrology applications in high-volume manufacturing.

FIG. 8B depicts a composite target formed on a substrate according to known practice. The composite target comprises four gratings 842 to 845 positioned closely together so that they will all be within an illumination spot 840. Imaging lens 802 provides an image plane on detector 112 where an image of target T will be focused. Only a selected one of the first orders in the diffraction spectrum contributes to the formation of the image, while the other is excluded by the aperture of the objective lens or by field stop 130. Consequently, each "image" is not a conventional image in which the grating lines can be resolved. (To form a conventional image requires at least two diffraction orders to interfere.) Rather, when the lock-in image detector 112 is synchronized with the beat frequency $\Delta\omega_1$, each grating is rendered as a patch of light, whose intensity depends on the energy diffracted into the selected portion of the diffraction spectrum.

In an example dedicated to overlay measurement, gratings 842 to 845 are themselves overlay gratings comprising overlying gratings that are patterned in different layers of the semiconductor device formed on substrate W. Gratings 842 to 845 may have differently biased overlay offsets in order to facilitate measurement of overlay between the layers in which the different parts of the composite gratings are formed. Gratings 842 to 845 may also differ in their orientation, as shown, so as to diffract incoming radiation in X and Y directions. In one example, gratings 842 and 844 are X-direction gratings with biases of +d and −d, respectively. Gratings 843 and 845 are Y-direction gratings with offsets +d and −d respectively. Many variations of target design and biasing schemes are known and applicable as desired. While four gratings are illustrated, another embodiment might require a larger matrix to obtain the desired accuracy. The targets can be adapted so that measurement of their asymmetry can be used to obtain a measurement of parameters other than overlay, as already mentioned. Examples of such parameters are focus and dose in the lithographic process.

FIG. 8C shows examples of an amplitude image (846-A) and phase image (846-φ) that may be detected by the detector 112, using the target of FIG. 8B and an aperture plate 128 also shown in FIG. 8C, in the apparatus of FIG. 8A. The dark rectangle represents the field of the image on detector 112, within which the illuminated spot 140 on the substrate is imaged into a corresponding circular area 850. Within this, rectangular areas 852-855 represent the "images" of the small target gratings 842 to 845. If the gratings are located in product areas, product features may also be visible in the periphery of this image field. Image processor and controller PU processes these images 846-A and 846-φ using pattern recognition to identify the separate images 852 to 855 of gratings 842 to 845. Once the separate images of the gratings have been identified, properties such as average intensity and phase and amplitude of the optical field can be retrieved from the measurement signals as described above, for each grating. The measured intensity/amplitude and/or phase can be compared between images taken with different target orientation or imaging mode or illumination modes, to obtain a measurement of asymmetry in each grating. By comparing the asymmetries for the different biased gratings, the processing unit PU or separate computer can calculate a measure of overlay or parameters of the lithographic process.

For example, overlay measurement results according to known practice are obtained by comparing the measured signals for a given grating to infer an asymmetry in the grating, and asymmetry in an overlay grating can be used as an indicator of overlay error.

Figure 9:
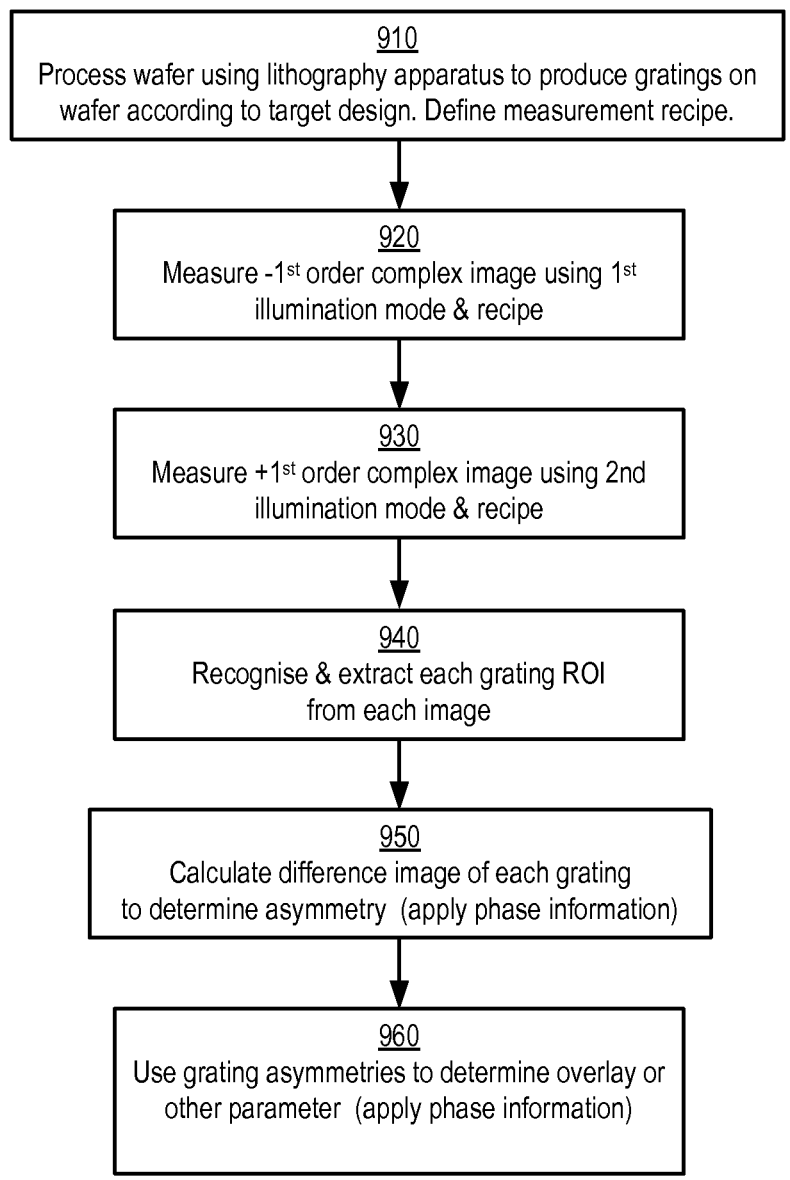
FIG. 9 depicts an example process for determining overlay or other performance parameters using dark-field imaging in the apparatus of FIG. 8A.

FIG. 9 illustrates a basic method of measuring overlay using the apparatus and targets described above. The method in this example is based on the method described in application US 2011027704 using the apparatus of FIGS. 3 and 4. In principle, overlay error between the two layers containing the component gratings of FIG. 8B is measured through asymmetry of the gratings, as revealed by comparing their intensities in the +1 order and 1 order dark field images. At step 910, the substrate, for example a semiconductor wafer, is processed through the lithographic cell of FIG. 2 one or more times, to create a structure including overlay gratings 842-845 that form a metrology target.

At 920, using the metrology apparatus of FIG. 8, and with lock-in image detector 112 synchronized with the beat frequency $\Delta\omega_1$, a (complex) image of the gratings 842-845 is obtained using only one of the first order diffracted beams (say −1). Then, whether by changing the illumination mode, or changing the imaging mode, or by rotating substrate W by 180° in the field of view of the metrology apparatus, a second (complex) image of the gratings using the other first order diffracted beam (+1) can be obtained (step 930). Consequently the +1 diffracted radiation for each grating is captured in the second image. It is a matter of design choice whether all the gratings 842-845 can be captured in each image, or whether the apparatus or substrate need to be moved so as to capture the gratings in separate images. In either case, it is assumed that first and second images of all the component gratings are captured via lock-in image detector 112.

In step 940, a region of interest (ROI, see FIG. 8C) is carefully identified within the image of each component grating, from which intensity levels will be measured. This is done because, particularly around the edges of the individual grating images, intensity values can be highly dependent on process variables such as resist thickness, composition, line shape, as well as edge effects generally.

Having identified the ROI for each individual grating and measured its intensity across the ROI, the asymmetry of the grating structure, and hence overlay error, can then be determined. As described in the prior applications, this is done by the image processor and controller PU in step 950 comparing the amplitude/intensity values and/or phase values obtained for +1 and −1 orders for each image 852-855 to identify any difference in their intensity. The intensity difference is calculated at step 950 to obtain a measurement of asymmetry for each grating. At step 960, from the asymmetry measurements and from knowledge of the overlay biases of the gratings, a processor calculates overlay error (or other parameter of interest) in the vicinity of the target T.

In a manner similar to that explained for FIG. 7, phase information obtained through lock-in image detector 112 can be combined with amplitude and/or intensity information to improve the accuracy of calculating a measurement of the parameter of interest.

The phase information also allows modeling of a 'filtered' signal in the pupil plane. The signal measured in the image plane may be Fourier filtered and a 'filtered' signal in the pupil plane may then be modeled. The modeling may be performed by the image processor and controller PU. Reconstruction of a filtered signal in the pupil plane improves the measurement quality in case, for instance, of target structures close to product structures or in case of inhomogeneities outside the region of interests. The phase information can be used to computationally infer and counteract focus errors during data post processing. The measurement quality is then further improved.

Figure 10A:
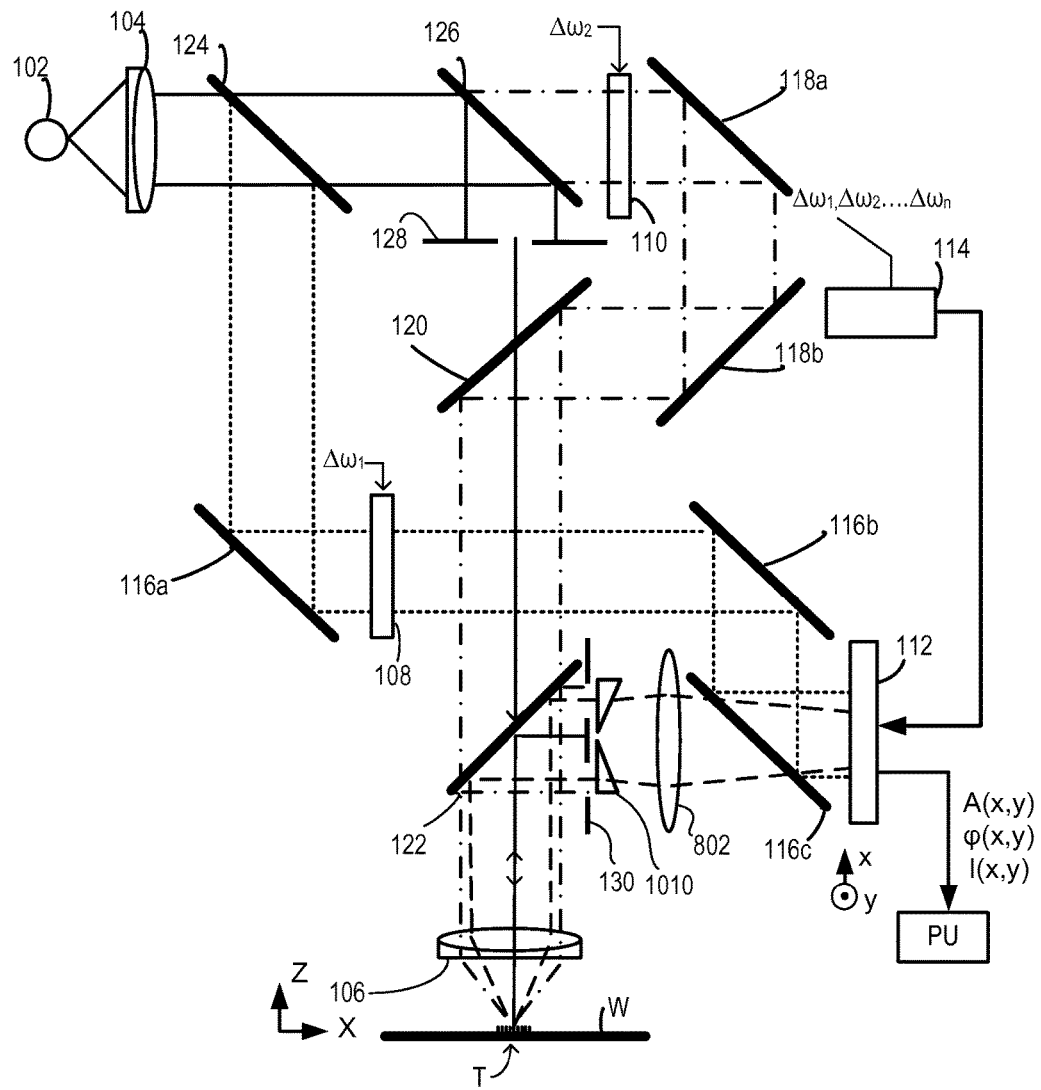
FIGS. 10A and 10B are schematic diagrams of an inspection apparatus including a lock-in image detector according to another embodiment of the invention, adapted for darkfield imaging metrology with small targets.

FIG. 10A shows another example of dark-field imaging inspection apparatus. The example of FIG. 10A is similar to that of FIG. 8, but modified to capture both +1 and −1 order images on different sections of the lock-in image detector simultaneously. This modification is based on an invention described in published patent application US2011102753 A1, the contents of which are hereby incorporated by reference.

Figure 10B:
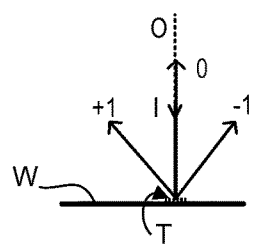

In this configuration, modified aperture plate 128 is selected to provide illumination only at the center of the illumination pupil. As shown in FIG. 10B, this means that incident ray I has normal incidence on target T, leading to the first order diffracted beams being radially either side of the optical axis O, while the zeroth order beam travels along the collection path and along the optical axis O. A modified field stop 130 filters out all but the first order diffracted beams.

Each of the +1 and −1 diffraction orders that pass through field stop 130 may be subsequently diverged by respective optical wedges 1010. This allows the separation of the two first order diffracted beams from each other so that they create a "double vision" effect. Thus the opposite portions of the diffraction spectrum are captured at different places on the detector and can be extracted and processed separately. In this way, only a single imaging step is required to obtain an asymmetry measurement. The apparatus of FIG. 10A comprises optical wedges 1010 aligned along the x-axis to separate the +1 and −1 diffraction orders in the x direction. Alternatively, optical wedges 1010 may be aligned along the y-axis to separate the +1 and −1 diffraction orders in the y direction, or a set of four optical wedges 1010 may be used with one of the optical wedges 1010 being aligned along the x-axis and the other along the y-axis, separating the +1 and −1 diffraction orders in the x and y directions.

Intensity normalization can be performed at a convenient time by setting the lock-in frequency to $\Delta\omega_2-\Delta\omega_1$, in the same manner as described above for the process of FIG. 6.

Variations

The illumination path used to obtain the diffraction pattern may also include a frequency shifter, instead of or in addition to shifting the frequency of the reference beam. Where both the diffraction signal and the reference beam are frequency-shifted, the resulting beat frequency value, generated by for example interference between the frequency-shifted illumination beam and the frequency-shifted first reference beam, may then be reduced to a lower value, even a few hertz. A lower frequency may permit the use of image sensor having more relaxed specifications for its acquisition frequency. This lower acquisition frequency may be less suitable however for use in applications not requiring such a high measurement throughput.

In the apparatus of FIG. 8 the first reference beam is focused onto detector 112 by imaging lens 802 placed after mirror 116c and before detector 112. By contrast, in the apparatus of FIG. 10A the first reference beam is directed to detector 112 by mirror 116c placed after imaging lens 802 and before detector 112. Either arrangement may be implemented in a practical instrument, depending on the application.

Note that in the apparatus of FIGS. 3, 8 and 10 an attenuating device (not shown), for instance a neutral density filter, may be placed somewhere in the first reference path to adjust the intensity of the frequency-shifted first reference beam to be compatible with the intensity of the diffraction signal in a particular case. The degree of attenuation can be made variable. For example by a motorized neutral density filter wheel.

Focus correction may be achieved by analyzing interference patterns created by interference between 0 and first orders diffracted beams.

Figure 11:
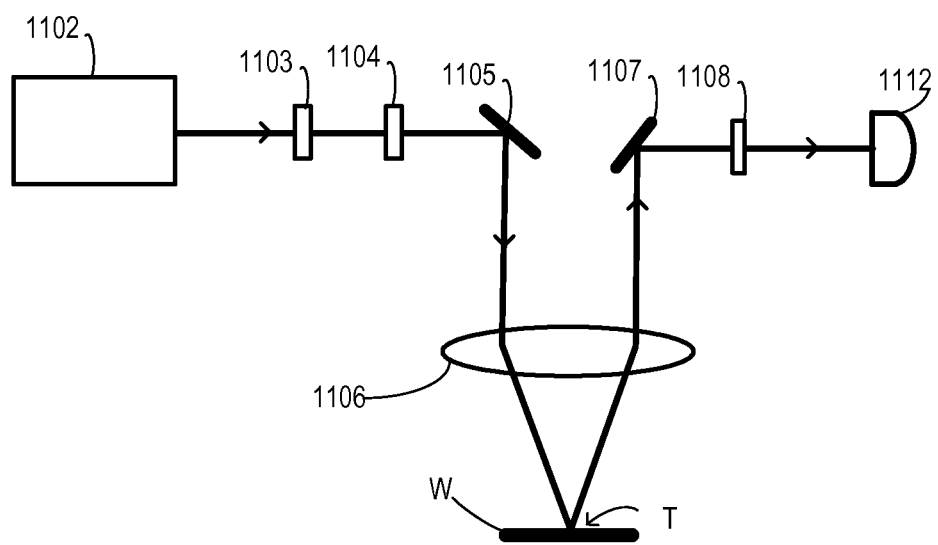
FIG. 11 illustrates an inspection apparatus in which a lock-in imaging detector is used to perform ellipsometry or polarimetry.

FIG. 11 shows use of modulation of polarization with a synchronized lock-in imaging detector, to perform polarimetric and ellipsometric measurements. This may be a stand-alone instrument, but may also be an optional mode of operation for performed using the inspection apparatus 100 of FIG. 3, 8 or 10. An illumination beam generated by radiation source 1102 may be polarized by a polarizing element 1103. A modulating element 1104 periodically modulates the polarization state of the illumination beam at a high frequency. This modulating element can be placed for example after the polarizing element 1103. The modulating element may be achieved a rotating polarization element (e.g. rotating polarizer, EOM etc.). The illumination beam is then used to illuminate the target T via optical component 1105 and microscope objective lens 1106. Since the polarization of the illumination beam is rotating at the frequency of the polarization rotating element, the light diffracted from the target, directed to lock-in detector 1112 via optical component 1107, also contains time-varying components of intensity and/or polarization that are varying at the same frequency. By introducing a fixed analyzer 1108 into inspection apparatus 100, for example before the lock-in detector 1112, by locking detector 1112 at the rotation frequency the amplitude and phase of the signal can be extracted. The amplitude and phase of the signal measured can then be used to extract the polarimetric parameters of the target. Complex image data in this example may for example represent the amplitude and angle of a polarization vector.

The setup can work with a fixed polarizer and a rotating analyzer as well. Instead of a rotating polarizer an electro-optic modulator may be used.

CONCLUSION

The method and associated inspection apparatus disclosed herein enable one or more of the following benefits.

Measurement of the far-field diffraction pattern of a scattering target is achieved by implementing a phase-sensitive heterodyne interferometric technique. Measurement of the far-field diffraction pattern allows retrieval of, for example, the diffracted signal intensity as well as the amplitude and phase of the associated optical field. This opens the possibility to perform a complete target reconstruction based on the measured complex far-field diffraction pattern of the scattering target. The accuracy of, for example, reconstruction processes (e.g. CD reconstruction or complete target reconstruction) would then be increased.

Intensity based scatterometers require bigger targets in order to retrieve critical metrology parameters (e.g. CD, Overlay and focus) from a measured light intensity. The techniques disclosed herein enable full-field measurement, facilitating the resolution of the ill-posed inverse scattering problem. A well-defined and more accurate solution to the inverse problem (scattered field to scattering target) can be delivered. This enables significant reduction of the space required for placing metrology targets on wafers.

In examples where asymmetry is measured and used with special targets directly to calculate measurements parameters of interest without performing reconstruction, the availability of phase information allows the calculated measurements to be less sensitive to variation in other parameters of the shape or the processing. Phase information can be used within the calculation of the parameter of interest, or can be used to apply a correction to the calculated value.

The ability to provide high resolution and accurate measurements is an essential challenge in metrology. A metrology system is subject to many noise sources (e.g. optical noise sources, electronic noise sources, mechanical noise sources). A general method for noise reduction is to use a reference detector (e.g. photodiode) to measure intensity fluctuations (delivering a reference signal) and, then, to use the reference signal to reduce noise in a measured signal of interest. However the performance of this general method is limited due to difference in the optical, electronic and mechanical components of the reference path, when compared to the path of the signal of interest. The provision of a second reference beam as disclosed above allows the same beam path to be used for both the reference path as well as the signal of interest. One detector may be used with appropriate frequency references to measure both the signal of interest and the reference signal. Furthermore, by making measurements based on heterodyne interferometric technique, it is possible to remove DC noise sources.

A metrology apparatus based on heterodyne interferometric technique, allows to significantly reduce the exposure dose (i.e. low optical intensity for target illumination) and to achieve a same SNR (signal to noise ratio), when coupled to a higher power "local oscillator" (i.e. the first reference beam). This can be used for example to obtain an improved SNR without the increase of the optical dose and/or the integration time. This would allow measurements of dark wafers (low scattering wafers) by increasing the power of the reference beam. As mentioned above, a motorized ND filter can be added to make the reference beam tunable in intensity.

Further embodiments according to the invention are provided in the below numbered clauses:

1. An inspection apparatus for measuring properties of a targets structure, the apparatus comprising a radiation source, and an image detector in combination with an optical system, the optical system defining the following beam paths:
   an illumination path for receiving radiation from the radiation source, forming a beam of illuminating radiation having a selected illumination profile and focusing said illuminating radiation onto a target on a substrate;
   a collection path for collecting diffracted radiation from said target and delivering a selected portion of the diffracted radiation to the image detector; and
   a reference path for receiving radiation from the radiation source and delivering a beam of reference radiation to the image detector so as to interfere with the diffracted radiation,
   wherein the image detector comprises an array of pixels for capturing two-dimensional images,
   wherein at least one of said illumination path and said reference path includes a device for shifting an optical frequency of the reference radiation so that the intensity of radiation at the image detector includes a time-varying component having a characteristic frequency corresponding to a difference between the frequencies of the diffracted radiation and the reference radiation,
   and wherein said image detector comprises a lock-in image detector operable with reference to said characteristic frequency to record for each pixel information representing both amplitude and phase of said time-varying component.

2. An inspection apparatus as described in clause 1 wherein said illumination path includes a device to define a non-uniform illumination profile across an illumination pupil of the optical system.

3. An inspection apparatus as described in clause 1 or 2 wherein said collection path includes a field stop in a collection pupil plane, the field stop in operation passing to selected portions only of a diffraction spectrum of the target.

4. An inspection apparatus as described in clause 3 wherein said reference path bypasses said field stop to illuminate the image detector with said reference radiation.

5. An inspection apparatus as described in any preceding clause further comprising a processor for processing the recorded amplitude and phase information to calculate a measurement of a property of the target.

6. An inspection apparatus as described in clause 5 wherein said optical system is operable to record separately amplitude and phase information from at least two selected portions of a diffraction spectrum of the target, the processor being arranged to calculate a measurement of a property of the target using the recorded amplitude and phase information from at least two selected portions.

7. An inspection apparatus as described in clause 6 wherein said at least two selected portions comprises opposite portions of the diffraction spectrum and said property is asymmetry.

8. An inspection apparatus as described in clause 7 wherein the apparatus is operable to calculate measurements of asymmetry for multiple targets, and wherein said processor is further arranged to calculate using said measurements and known characteristics of the targets a performance parameter of a lithographic process used to form the targets.

9. An inspection apparatus as described in clause 8 wherein said optical system in the collection path includes imaging optics arranged to deliver diffracted radiation from different locations on the target to different locations on the image detector, and the processor is arranged to extract amplitude and phase information for multiple targets from pixels in different regions of the image detector.

10. An inspection apparatus as described in clause 6, 7 or 8 wherein the optical system in said collection path is arranged to deliver the at least two selected portions of the diffraction spectrum to different locations on said image detector, and the processor is arranged to extract amplitude and phase information for each portion from pixels in corresponding regions of the image detector.

12. An inspection apparatus as described in clause 10 wherein said optical system in the collection path includes imaging optics is arranged to deliver diffracted radiation from different locations on the target to different locations on the image detector, and further includes beam diverting optics arranged so that for each location on the target the selected portions of the diffracted radiation are directed to different locations on the target, and the processor is arranged to extract amplitude and phase information for each location on the target and each selected portion of the diffracted radiation from pixels in corresponding regions of the image detector.

13. An inspection apparatus as described in any of clauses 5 to 12 wherein the optical system in said collection path is arranged to form an image of a pupil plane of the collection path on the detector, such that the image detector records a diffraction pattern representing one or more selected portions of the diffraction spectrum of the target, and the processor is arranged to compare the recorded amplitude and phase information for one or more portions of the diffraction spectrum with modeled amplitude and phase information corresponding to a candidate target structure.

14. An inspection apparatus as described in any of clauses 5 to 13 wherein the optical system in said collection path is arranged to deliver at least two selected portions of the diffraction spectrum to the image detector in separate image capture operations, and the processor is arranged to combine information from at least two image capture operations to calculate a property of the target.

15. A method for measuring properties of a targets structure, the method comprising the steps:
(a) illuminating a target on a substrate with an illuminating radiation emitted from a radiation source and having a selected illumination profile;
(b) collecting diffracted radiation from said target and delivering a selected portion of the diffracted radiation to an image detector comprising an array of pixels for capturing two-dimensional images;
(c) delivering a beam of reference radiation emitted from the radiation source to the image detector so as to interfere with the diffracted radiation,
wherein steps (a) and (c) include introducing an optical frequency shift between the reference radiation and the illuminating radiation so that the intensity of radiation at the image detector includes a time-varying component having a characteristic frequency corresponding to the frequency shift; and wherein step (b) includes operating the image detector as a lock-in image detector at the characteristic frequency, to record two-dimensional images both amplitude and phase of the time-varying component.

16. The method of clause 15 wherein the diffracted radiation is measured in a pupil plane.

17. The method of clause 15 wherein the diffracted radiation is measured in an image plane imaged by imaging optics.

18. The method of clause 15, 16 or 17 further comprising the step:
(d) processing the recorded amplitude and phase information to calculate a measurement of a property of the target.

19. The method of clause 18 wherein step (d) comprises processing separately amplitude and phase information from at least two selected portions of a diffraction spectrum of the target to calculate a measurement of a property of the target using the recorded amplitude and phase information from at least two selected portions.

20. The method of clause 19 wherein the at least two selected portions comprise opposite portions of the diffraction spectrum and said property is asymmetry.

21. The method of clause 20 wherein in step (d) said asymmetry is calculated from amplitude information of the selected portions of the diffraction spectrum, while said phase information is used to calculate and apply a correction before and/or after calculating asymmetry.

22. The method of clause 20 or 21 wherein steps (a) to (d) are repeated to obtain measurements of asymmetry for multiple targets, the method further comprising the step:

(e) using said measurements and known characteristics of the targets to calculate a measurement of a performance parameter of a lithographic process used to form the targets.

23. A method as described in clause 22 wherein said performance parameter of the lithographic process is one of overlay, focus and dose.

24. The method of clause 22 or 23 wherein said phase information is used in the calculation of said performance parameter in step (e).

25. A method of manufacturing devices wherein device features and metrology targets are formed on a series of substrates by a lithographic process, wherein properties of the metrology targets on one or more processed substrates are measured by a method as described in any of clauses 18 to 24, and wherein the measured properties are used to adjust parameters of the lithographic process for the processing of further substrates.

26. A computer program product containing one or more sequences of machine-readable instructions for implementing the step (d) of a method of any of clauses 18 to 24.

27. A computer program product containing one or more sequences of machine-readable instructions for implementing the steps (d) and (e) of a method of any of clauses 22 to 24.

Although specific reference may be made in this text to the use of inspection apparatus in the manufacture of ICs, it should be understood that the inspection apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. Furthermore, parts of the apparatus may be implemented in the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. An inspection apparatus for measuring properties of a target structure, comprising:
   a radiation source;
   an image detector; and
   an optical system, the optical system defining the following beam paths:
      an illumination path for receiving radiation from the radiation source, forming a beam of illuminating radiation having a selected illumination profile and focusing said illuminating radiation onto a target on a substrate;
      a collection path for measuring collecting diffracted radiation from said target and delivering a selected portion of the diffracted radiation to the image detector; and
      a reference path for receiving radiation from the radiation source and delivering a beam of reference radiation to the image detector so as to interfere with the diffracted radiation,
   wherein the image detector comprises an array of pixels for capturing two-dimensional images,
   wherein at least one of said illumination path and said reference path includes a device for shifting an optical frequency of the reference radiation so that the intensity of radiation at the image detector includes a time-varying component having a characteristic frequency corresponding to a difference between the frequencies of the diffracted radiation and the reference radiation, and
   wherein said image detector comprises a heterodyne lock-in image detector operable with reference to said characteristic frequency to record for each pixel information representing both amplitude and phase of said time-varying component and such that amplitude and phase of multiple angles from the target are measured simultaneously.

2. The inspection apparatus as claimed in claim 1, further comprising a processor for processing the recorded amplitude and phase information to calculate a measurement of a property of the target.

3. The inspection apparatus as claimed in claim 2, wherein said optical system is operable to record separately amplitude and phase information from at least two selected portions of a diffraction spectrum of the target, the processor being arranged to calculate a measurement of a property of the target using the recorded amplitude and phase information from at least two selected portions.

4. The inspection apparatus as claimed in claim 3, wherein said at least two selected portions comprise opposite portions of the diffraction spectrum and said property is asymmetry.

5. The inspection apparatus as claimed in claim 3, wherein the optical system in said collection path is arranged to deliver the at least two selected portions of the diffraction spectrum to different locations on said image detector, and the processor is arranged to extract amplitude and phase information for each portion from pixels in corresponding regions of the image detector.

6. The inspection apparatus as claimed in claim 5, wherein said optical system in the collection path includes imaging optics arranged to deliver diffracted radiation from different locations on the target to different locations on the image detector, and further includes beam diverting optics arranged so that for each location on the target the selected portions of the diffracted radiation are directed to different locations on the target, and the processor is arranged to extract amplitude and phase information for each location on the target and each selected portion of the diffracted radiation from pixels in corresponding regions of the image detector.

7. The inspection apparatus as claimed in claim 2, wherein the optical system in said collection path is arranged to form an image of a pupil plane of the collection path on the detector, such that the image detector records a diffraction pattern representing one or more selected portions of the diffraction spectrum of the target, and the processor is arranged to compare the recorded amplitude and phase information for one or more portions of the diffraction spectrum with modeled amplitude and phase information corresponding to a candidate target structure.

8. The inspection apparatus as claimed in claim 2, wherein the optical system in said collection path is arranged to deliver at least two selected portions of the diffraction spectrum to the image detector in separate image capture operations, and the processor is arranged to combine information from at least two image capture operations to calculate a property of the target.

9. The inspection apparatus as claimed in claim 1, wherein different diffraction orders are measured simultaneously.

10. The inspection apparatus as claimed in claim 1, wherein the optical system is a scanning optical system.

11. A method for measuring properties of a target structure, the method comprising the steps:
   (a) illuminating a target on a substrate with an illuminating radiation emitted from a radiation source and having a selected illumination profile;
   (b) collecting diffracted radiation from said target and delivering a selected portion of the diffracted radiation to an image detector comprising an array of pixels for capturing two-dimensional images;
   (c) delivering a beam of reference radiation emitted from the radiation source to the image detector so as to interfere with the diffracted radiation,
   wherein steps (a) and (c) include introducing an optical frequency shift between the reference radiation and the illuminating radiation so that the intensity of radiation at the image detector includes a time-varying component having a characteristic frequency corresponding to the frequency shift; and
   wherein step (b) includes operating the image detector as a heterodyne lock-in image detector at the characteristic frequency, to record two-dimensional images representing both amplitude and phase of the time-varying component, and such that amplitude and phase of multiple angles from the target are measured simultaneously.

12. The method of claim 11, wherein the diffracted radiation is measured in a pupil plane.

13. The method of claim 11, wherein the diffracted radiation is measured in an image plane imaged by imaging optics.

14. The method of claim 11, further comprising the step:
(d) processing the recorded amplitude and phase information to calculate a measurement of a property of the target.

15. The method of claim 14, wherein step (d) comprises processing separately amplitude and phase information from at least two selected portions of a diffraction spectrum of the target to calculate a measurement of a property of the target using the recorded amplitude and phase information from at least two selected portions.

16. The method of claim 15, wherein the at least two selected portions comprise opposite portions of the diffraction spectrum and said property is asymmetry.

17. The method of claim 16, wherein in step (d) said asymmetry is calculated from amplitude information of the selected portions of the diffraction spectrum, while said phase information is used to calculate and apply a correction before and/or after calculating asymmetry.

18. The method of claim 16, wherein steps (a) to (d) are repeated to obtain measurements of asymmetry for multiple targets, the method further comprising the step:
(e) using said measurements and known characteristics of the targets to calculate a measurement of a performance parameter of a lithographic process used to form the targets.

19. A method as claimed in claim 18, wherein said performance parameter of the lithographic process is one of overlay, focus and dose.

20. The method of claim 18, wherein said phase information is used in the calculation of said performance parameter in step (e).

21. A method of manufacturing devices wherein device features and metrology targets are formed on a series of substrates by a lithographic process, wherein properties of the metrology targets on one or more processed substrates are measured by a method as claimed in claim 14, and wherein the measured properties are used to adjust parameters of the lithographic process for the processing of further substrates.

22. A computer program product comprising non-transitory computer readable medium having one or more sequences of instructions for implementing the step (d) of a method of claim 14.

23. The method of claim 11, further comprising simultaneously measuring different diffraction orders.

24. The method of claim 11, wherein illuminating the target with the illuminating radiation further comprises scanning the target.

* * * * *